US009717676B2

(12) United States Patent
Gartstein et al.

(10) Patent No.: US 9,717,676 B2
(45) Date of Patent: *Aug. 1, 2017

(54) AMINO SILICONE NANOEMULSION

(71) Applicant: The Procter & Gamble Company, Cincinnati, OH (US)

(72) Inventors: Vladimir Gartstein, Mason, OH (US); William Richard Mueller, Cincinnati, OH (US); Charles Raymond Degenhardt, Cincinnati, OH (US); Hiroshi Oh, Cincinnati, OH (US); Steven Daryl Smith, Fairfield, OH (US); Nicholas David Vetter, Cleves, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 230 days.

This patent is subject to a terminal disclaimer.

(21) Appl. No.: 14/312,714

(22) Filed: Jun. 24, 2014

(65) Prior Publication Data

US 2015/0030643 A1 Jan. 29, 2015

Related U.S. Application Data

(60) Provisional application No. 61/858,641, filed on Jul. 26, 2013.

(51) Int. Cl.
| | | |
|---|---|---|
| *A61K 8/898* | (2006.01) | |
| *C11D 17/00* | (2006.01) | |
| *C11D 3/37* | (2006.01) | |
| *A61Q 19/10* | (2006.01) | |
| *A61K 8/06* | (2006.01) | |
| *A61Q 5/12* | (2006.01) | |
| *A61Q 5/02* | (2006.01) | |
| *D06M 13/10* | (2006.01) | |
| *A61K 8/36* | (2006.01) | |
| *A61K 8/39* | (2006.01) | |
| *A61K 8/34* | (2006.01) | |
| *A61K 8/86* | (2006.01) | |
| *A61K 8/02* | (2006.01) | |
| *A61Q 5/06* | (2006.01) | |

(52) U.S. Cl.
CPC ............ *A61K 8/898* (2013.01); *A61K 8/0208* (2013.01); *A61K 8/06* (2013.01); *A61K 8/345* (2013.01); *A61K 8/36* (2013.01); *A61K 8/39* (2013.01); *A61K 8/86* (2013.01); *A61Q 5/02* (2013.01); *A61Q 5/12* (2013.01); *A61Q 19/10* (2013.01); *C11D 3/3742* (2013.01); *C11D 17/0021* (2013.01); *D06M 13/10* (2013.01); *A61K 2800/21* (2013.01); *A61Q 5/06* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 3,748,275 A | | 7/1973 | Bernheim et al. |
| 4,559,227 A | * | 12/1985 | Chandra .................. A61K 8/40 424/59 |
| 4,620,878 A | | 11/1986 | Gee |
| 5,000,861 A | * | 3/1991 | Yang ......................... C08J 3/03 252/8.62 |
| 5,244,598 A | | 9/1993 | Merrifield et al. |
| 5,712,343 A | | 1/1998 | Geck et al. |
| 5,827,921 A | | 10/1998 | Osawa et al. |
| 6,153,569 A | * | 11/2000 | Halloran ................. A61K 8/068 424/70.12 |
| 6,177,511 B1 | | 1/2001 | Dauth et al. |
| 6,303,686 B1 | | 10/2001 | Kitahara et al. |
| 7,319,119 B2 | | 1/2008 | Mahr et al. |
| 7,763,240 B2 | | 7/2010 | Anderson et al. |
| 7,833,961 B2 | | 11/2010 | Declerq et al. |
| 7,928,055 B2 | | 4/2011 | Gizaw et al. |
| 8,633,146 B2 | | 1/2014 | Wang et al. |
| 8,637,442 B2 | | 1/2014 | Wang et al. |
| 8,778,866 B2 | | 7/2014 | Fernandez Martinez |
| 9,080,130 B2 | | 7/2015 | Sivik et al. |
| 2001/0028887 A1 | * | 10/2001 | Douin ...................... A61K 8/06 424/401 |
| 2002/0098215 A1 | * | 7/2002 | Douin ...................... A61K 8/06 424/401 |
| 2003/0147842 A1 | * | 8/2003 | Restle .................... A61K 8/416 424/70.122 |
| 2003/0157049 A1 | * | 8/2003 | Gawtrey ................ A61K 8/731 424/70.122 |
| 2007/0042124 A1 | | 2/2007 | Matsumura et al. |

(Continued)

FOREIGN PATENT DOCUMENTS

| | | |
|---|---|---|
| CA | 2129911 | 2/1995 |
| CN | 102031698 A | 4/2011 |

(Continued)

OTHER PUBLICATIONS

STN Accession No. 2011:18170 CAPLUS (Jan. 6, 2011).*
Dow Chemical Company Technical Data Sheet: Hexyl CELLOSOLVE Solvent & Hexyl Carbitol Solvent (Aug. 2001).*
Lim, Yeon Hee, Chung Hee Park, and Jooyoun Kim. "Hair conditioning effect of amino silicone softeners in varied treatment conditions." Fibers and Polymers 11.3 (2010): 507-515.*

(Continued)

*Primary Examiner* — Bethany Barham
*Assistant Examiner* — Peter Anthopolos
(74) *Attorney, Agent, or Firm* — Jason J Camp

(57) ABSTRACT

The present invention relates to amino silicone nanoemulsions. More specifically, the present invention relates to amino silicone nanoemulsions that may be used to protect surfaces from being soiled or wetted.

22 Claims, No Drawings

(56) References Cited

U.S. PATENT DOCUMENTS

| | | |
|---|---|---|
| 2008/0209645 A1 | 9/2008 | Carrillo et al. |
| 2008/0242584 A1 | 10/2008 | Wahl et al. |
| 2009/0042765 A1 | 2/2009 | Gizaw et al. |
| 2009/0226381 A1 | 9/2009 | Maillefer et al. |
| 2011/0159301 A1 | 6/2011 | Wakamatsu et al. |
| 2012/0058062 A1 | 3/2012 | Carson |
| 2012/0071382 A1 | 3/2012 | Danziger |
| 2012/0077725 A1 | 3/2012 | Wang et al. |
| 2012/0321679 A1 | 12/2012 | Morita et al. |
| 2013/0109612 A1 | 5/2013 | Corona, III et al. |
| 2013/0165566 A1 | 6/2013 | Merget et al. |
| 2013/0177517 A1 | 7/2013 | Merget et al. |

FOREIGN PATENT DOCUMENTS

| | | | |
|---|---|---|---|
| EP | 646618 | | 4/1995 |
| EP | 0739928 A2 | | 10/1996 |
| EP | 646618 B | | 12/1996 |
| EP | 0972789 A1 | | 1/2000 |
| EP | 1746153 A1 | | 1/2007 |
| JP | 11292977 | | 10/1999 |
| JP | 2006193635 A | | 7/2006 |
| JP | 2006297272 A | | 11/2006 |
| JP | 2006328587 A | | 12/2006 |
| JP | 2006342460 A | | 12/2006 |
| JP | 2007016116 A | | 1/2007 |
| JP | 20111419 A | | 1/2011 |
| JP | 2011001419 A | * | 1/2011 |
| WO | WO 2008/142998 A1 | | 11/2008 |
| WO | WO2011042409 A2 | | 4/2011 |

OTHER PUBLICATIONS

Xu, Yingjun, et al. "Application performance and surface morphologies of amino polysiloxanes with different amino values and amino types." Journal of Applied Polymer Science 119.4 (2011): 2326-2333.*

International Search Report and Written Opinion dated Nov. 21, 2014, 27 pgs.

Akzonobel: "Technical Information Surface Chemistry, HLB Emulsification", Jan. 1, 2011, pp. 1-15, XP055153871, http:V/www.surface.akzonobel.com.

International Search Report and Written Opinion dated Dec. 9, 2014, 17 pgs.

Yong-Lai Zhang et al., "Solvothermal Synthesis of Nanoporous Chalk for Painting Superhydrophobic Surfaces", Langmuir article, ACS Publications, revised Aug. 23, 2011, 6 pages.

T. Dikić et al, "Self-Replenishing Surfaces", Advanced Materials 2012, 24, pages 3701-3704.

U.S. Appl. No. 14/312,717, filed Jun. 24, 2014, Vladimir Gartstein et al.

* cited by examiner

AMINO SILICONE NANOEMULSION

FIELD OF THE INVENTION

The present invention relates to amino silicone nanoemulsions. More specifically, the present invention relates to amino silicone nanoemulsions that may be used to protect surfaces from being soiled or wetted.

BACKGROUND OF THE INVENTION

Numerous attempts have been made to develop a treatment composition that provides protection of surfaces by repelling water and oil based soils from the surface. Fluoropolymers, such as those used in Scotchguard® from 3M, have become well established as soil-repellant molecules. However, fluoropolymers are not preferred due to environmental, and health and safety concerns, such as potential and possibility of persistent bioaccumulation and toxicity.

The combination of polyorganosiloxane fluids and silicone resins in attempts to treat hard or soft surfaces is also known. Silicone resins are highly cross-linked silicone materials that have very high viscosities. These materials are generally difficult to handle in a manufacturing environment and difficult to formulate with, given their high viscosities. And, incorporating compositions containing silicone resins into liquid-based and emulsion-based treatment formulations generally requires high energy processes.

And, an amino-modified silicone microemulsion that contains an amino-modified silicone and a high concentration of both ethylene glycol monoalkyl ether and nonionic surfactant, e.g., polyoxyalkylene branched decyl ether, is known; this amino-modified silicone nanoemulsion is described as transparent in appearance and having a small particle diameter.

Unfortunately, to date, the attempts at non-fluoropolymer protection of surfaces continue to demonstrate disadvantages, including low efficiency, difficulty in achieving the desired benefits at affordable cost and in a preferred format, processing and formulation challenges, and product instability. A continued need exists for a non-fluoropolymer technology that delivers depositable benefits to surfaces, such as water and oily soil repellency, in a convenient form and at a high efficiency.

SUMMARY OF THE INVENTION

The present invention attempts to solve one more of the needs by providing, in one aspect of the invention, an amino silicone nanoemulsion, which comprises a reduced concentration of solvent and surfactant. The amino silicone nanoemulsion comprises one or more amino silicone compounds; from about 0.1% to about 20% of a solvent, by weight of the amino silicone compound; from about 1% to about 40% of a surfactant, by weight of the amino silicone compound; and a protonating agent, where the sum of the solvent and the surfactant is less than about 50% by weight of said amino silicone compound and where the amino silicone nanoemulsion is substantially free of silicone resin.

The invention also relates to methods of making and using these amino silicone nanoemulsions.

Another aspect of the invention includes treatment compositions that comprise amino silicone nanoemulsions, which comprise reduced concentrations of solvent and surfactant, and the use thereof. Other aspects of the invention include methods of making treatment compositions comprising the amino silicone nanoemulsions and methods of treating surfaces with treatment compositions comprising the amino silicone nanoemulsions.

DETAILED DESCRIPTION OF THE INVENTION

Features and benefits of the various embodiments of the present invention will become apparent from the following description, which includes examples of specific embodiments intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein, the articles including "the," "a" and "an" when used in a claim or in the specification, are understood to mean one or more of what is claimed or described.

As used herein, the terms "include," "includes" and "including" are meant to be non-limiting.

As used herein, the terms "substantially free of" or "substantially free from" means that the indicated material is at the very minimum not deliberately added to the composition to form part of it, or, preferably, is not present at analytically detectable levels. It is meant to include compositions whereby the indicated material is present only as an impurity in one of the other materials deliberately included.

As used herein, the term nanoemulsion refers to thermal dynamically stable oil in water emulsions that have extremely small droplet sizes (below 350 nm, or typically below 250 nm). These materials have special properties, including optical translucency, very large dispersed phase surface-to-volume ratios and long term kinetic stability. Due to similarity in appearance, translucent nanoemulsions are sometimes confused with microemulsions, which belong to another class of stable (thermodynamically) and optically clear colloidal systems. Microemulsions are spontaneously formed by "solubilizing" oil molecules with a mixture of surfactants, co-surfactants and co-solvents. The required surfactant concentration in a microemulsion is several times higher than that in a nanoemulsion and significantly exceeds the concentration of the dispersed phase (generally, oil). Because of many undesirable side-effects caused by surfactants, this is disadvantageous or prohibitive for many applications. In addition, the stability of microemulsions is easily compromised by dilution, heating, or changing pH levels.

All cited patents and other documents are, in relevant part, incorporated by reference as if fully restated herein. The citation of any patent or other document is not an admission that the cited patent or other document is prior art with respect to the present invention.

In this description, all concentrations and ratios are on a weight basis of the cleaning composition unless otherwise specified.

The present invention encompasses an amino silicone nanoemulsion. The amino silicone nanoemulsion comprises one or more amino silicone compounds; from about 0.1% to about 20%, by weight of the amino silicone compound, of a solvent; from about 1% to about 30% by weight of the amino silicone compound of a surfactant; and a protonating agent, where the sum of the solvent and the surfactant is less than 50% by weight of said amino silicone compound and where the amino silicone nanoemulsion is substantially free of a silicone resin.

Known amino silicone microemulsions and methods for preparing amino silicone microemulsions employ high levels of solvent and nonionic surfactant (e.g., 12% ethylene glycol monohexyl ether per 100% of amino silicone and 40% polyoxyalkylene branched decyl ether per 100% of amino silicone), and/or require high energy in the form of heat or high shearing forces in order to obtain the desired nanoparticle size Without being bound by theory, it is believed that the presence of high levels of solvent and surfactant in the emulsion hinders the deposition of the amino silicone on the surface that is to be treated; amino silicone droplets in high-solvent and high-surfactant emulsions tend to stay in the emulsion, rather than deposit on the surface. This results in a poor delivery of any benefit, such as increased water repellency or oil repellency, to the surface. Such benefits may be measured as an increased time to wick on fabrics, a reduced dry-time on hair and/or an increased contact angle on a hard surface.

In contrast to conventional amino silicone microemulsions, the amino silicone nanoemulsions of the present invention comprise reduced levels of solvent and surfactant and may be obtained without the input of high energy. Yet, the amino silicone nanoemulsions disclosed herein provide a highly efficient deposition on a target surface. Benefits derived from this deposition may generally apply in the area of repellency of water and/or water-based compositions and/or oil and/or oil-based compositions, such as water-based stains and oily soils. Without being bound by theory, it is believed that the amino silicone nanoemulsions disclosed herein comprise self-assembled, spherical, positively charged amino silicone nano-particles (which contain reduced levels of solvent and surfactant). These self-assembled, spherical, positively charged nano-particles exhibit efficient deposition and controlled spreading, forming a structured film on a surface that provides the repellency benefit.

The average particle sizes of the disclosed nanoemulsions range from about 20 nm to about 350 nm, or about 20 nm to about 250 nm, or about 20 nm to about 200 nm, or about 30 nm to about 140 nm, or about 50 nm to about 100 nm. (as measured by Malvern Zetasizer Nano Series instrument.). The disclosed nanoemulsions are generally transparent or slightly milky in appearance.

Amino Silicone Compound

The amino silicone nanoemulsion of the present invention comprises from about 1% to about 45% of one or more amino silicone compounds, by weight of the nanoemulsion. In certain aspects, the amino silicone nanoemulsion comprises from about 5% to about 30% of the amino silicone compounds, by weight of the nanoemulsion. In other aspects, the amino silicone nanoemulsion comprises from about 10% to about 20% of the amino silicone compounds, by weight of the nanoemulsion.

The amino silicone compound may be represented by structural formula (1) below:

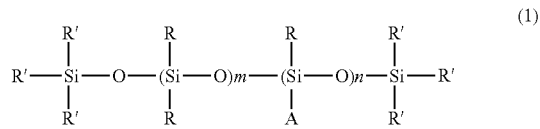

(1)

where each R group is independently selected from substituted or unsubstituted alkyl or aryl groups having 1-22 carbon atoms, each R' group is independently selected from substituted or unsubstituted alkyl or aryl groups having 1-22 carbon atoms, or monovalent groups represented by the formula: —OR$^3$, where R$^3$ is a hydrogen atom or a monovalent hydrocarbon group with 1-10 carbon atoms; m is a whole number from 20-1000, typically m is a whole number from 50-800; n is a whole number from 1-100, typically n is a whole number from 5-80.

A is a monovalent group represented by formula (2) below:

(2)

where each of R$^1$ and R$^2$ is independently selected from divalent hydrocarbon groups having 1-22 carbon atoms, more typically 1-8 carbon atoms, even more typically 1-4 carbon atoms. Suitable R$^1$ and R$^2$ groups include methylene groups, ethylene groups, trimethylene groups, tetramethylene groups, or other alkylene groups. In some aspects, each of R$^1$ and R$^2$ is a methylene group; a is a whole number from 0-4, typically a is a whole number from 0-2, more typically, a is 0 or 1.

One species of amino silicone compound may be used alone or two or more species may be used together.

Examples of suitable A groups include —CH$_2$—NH$_2$, —(CH$_2$)$_2$—NH$_2$, —(CH$_2$)$_3$—NH$_2$, —(CH$_2$)$_2$—NH—(CH$_2$)$_3$ NH$_2$, —(CH$_2$)$_3$—NH—(CH$_2$)$_2$NH$_2$, —(CH$_2$)$_3$—HN—(CH$_2$)$_3$NH$_2$, and —(CH$_2$)$_3$—NH—(CH$_2$)$_3$—NH—(CH$_2$)$_3$—NH$_2$.

In some aspects, in the amino silicone compound of formula (1), the ratio of m/n is less than about 100, typically m/n is less than about 90, more typically m/n is less than about 80.

In certain aspects, the amino silicone compound is represented by general formula (1), where each R is a methyl group, each R' is a methyl group, A is a propyl amino, and m/n is about 70.

In some aspects, in the amino silicone compound represented by general formula (1), from about 1% to about 20% of the terminal R' groups are monovalent groups represented by the formula: —OR$^3$, where R$^3$ is a hydrogen atom or a monovalent hydrocarbon group with 1-10 carbon atom.

The viscosity of the amino silicone compound is from about 10 mPa·s, at 25° C., or from about 50 mPa·s, to about 100,000 mPa·s, or to about 10,000 mPa·s. In certain aspects, the polyorgansiloxane compound has a viscosity of from about 200 mPa·s to about 500 mPa·s, at 25° C.

Silicone Resin

Typically, the amino silicone nanoemulsion of the present disclosure is substantially free of a silicone resin.

An example of a silicone resin is a mixture of polyorganosiloxane-silicone resins, where each of the one or more silicone resins of the polyorganosiloxane-silicone resin mixture contains at least about 80 mol % of units selected from the group consisting of units of the general formulas 3, 4, 5, 6:

(3),

(4),

(5),

(6), in which R$^4$ is selected from H, —OR, or —OH residues or monovalent hydrocarbon residues with 1 to 40 carbon atoms, optionally substituted with halogens, where at least 20 mol % of the units are selected from the group consisting of units of the general formulas 5 and 6, and a maximum of 10 wt % of the R$^4$ residues are —OR and —OH residues.

Solvent

The amino silicone nanoemulsion of the present invention comprises from about 0.1% to about 20% of one or more solvents, by weight of the amino silicone, provided that the amino silicone nanoemulsion comprises less than about 50%, or less than about 45%, or less than about 40%, or less than about 35%, or less than about 32% of solvent and surfactant combined, by weight of the amino silicone. In certain aspects, the amino silicone nanoemulsion comprises from about 0.1% to about 12% of one or more solvents, by weight of the amino silicone. In some aspects, the amino silicone nanoemulsion comprises from about 0.1% to about 5% of one or more solvents, by weight of the amino silicone. In other aspects, the amino silicone nanoemulsion comprises from about 1% to about 5% or from about 2% to about 5% of one or more solvents, by weight of the amino silicone.

The solvent is selected from monoalcohols, polyalcohols, ethers of monoalcohols, ethers of polyalcohols, or mixtures thereof. Typically, the solvent has a hydrophilic-lipophilic balance (HLB) ranging from about 6 to about 14. More typically, the HLB of the solvent will range from about 8 to about 12, most typically about 11. One type of solvent may be used alone or two or more types of solvents may be used together.

In some aspects, the solvent comprises a glycol ether, an alkyl ether, an alcohol, an aldehyde, a ketone, an ester, or a mixture thereof.

In some aspects, the solvent is selected from a monoethylene glycol monoalkyl ether that comprises an alkyl group having 4-12 carbon atoms, a diethylene glycol monoalkyl ether that comprises an alkyl group having 4-12 carbon atoms, or a mixture thereof. Suitable alkyl groups include butyl groups, hexyl groups, heptyl groups, octyl groups, 2-ethylhexyl groups, nonyl groups, decyl groups, undecyl groups, and dodecyl groups. In some aspects, the alkyl group is a hexyl group, e.g., diethylene glycol monohexyl ether or ethylene glycol monohexyl ether.

Suitable examples of monoethylene glycol monoalkyl ethers and diethylene glycol monoalkyl ethers include ethylene glycol monobutyl ether, ethylene glycol monohexyl ether, ethylene glycol monooctyl ether, ethylene glycol monodecyl ether, and ethylene glycol monododecyl etherdiethylene glycol monobutyl ether, diethylene glycol monohexyl ether, diethylene glycol monooctyl ether, diethylene glycol monodecyl ether, and diethylene glycol monododecyl ether. In some aspects, the solvent is ethylene glycol monohexyl ether, diethylene glycol monohexyl ether, or a mixture thereof.

In some aspects, the solvent comprises an ethylene glycol monoalkyl ether that comprises an alkyl group having 4-12 carbon atoms, a diethylene glycol monoalkyl ether that comprises an alkyl group having 4-12 carbon atoms, an ethylene glycol monohexyl ether, an ethylene glycol monobutyl ether, a diethylene glycol monohexyl ether, a diethylene glycol monobutyl ether, or combinations thereof.

Surfactant

The amino silicone nanoemulsion of the present invention comprises from about 1% to about 40% of one or more surfactants, by weight of the amino silicone, provided that the combined weight of the surfactant plus the solvent is less than about 50%, or less than about 45%, or less than about 40%, or less than about 35%, or less than about 32%, by weight of the amino silicone. In certain aspects, the amino silicone nanoemulsion comprises from about 1% to about 30%, or from about 1% to about 25%, or from about 1% to about 20% of one or more surfactants, by weight of the amino silicone. In some aspects, the amino silicone nanoemulsion comprises from about 5% to about 20% or from about 10% to about 20% of one or more surfactants, by weight of the amino silicone. The surfactant is selected from anionic surfactants, nonionic surfactants, cationic surfactants, zwitterionic surfactants, amphoteric surfactants, ampholytic surfactants, or mixtures thereof. In some aspects, the amino silicone nanoemulsion of the present disclosure comprises a nonionic surfactant, a cationic surfactant, or a mixture thereof. In certain aspects, the amino silicone nanoemulsion of the present disclosure comprises a nonionic surfactant. It is believed that surfactant, particularly nonionic surfactant, facilitates uniform dispersing of the amino silicone fluid compound and the solvent in water.

Nonionic Surfactants

Suitable nonionic surfactants useful herein may comprise any conventional nonionic surfactant. More specific examples of suitable nonionic surfactants include, for example, polyoxyethylene alkyl ethers, polyoxyethylene polyoxypropylene alkyl ethers or other polyoxyalkylene alkyl ethers; polyoxyethylene alkylphenyl ethers; polyoxyethylene alkyl esters; polyoxyethylene alkyl phenyl ether sorbitan esters; glycerin esters; sorbitan fatty acid esters; sucrose fatty acid esters or other polyhydric alcohol fatty acid esters; ethoxylated fatty acids; and ethoxylated fatty acid amides. In some aspects, the nonionic surfactant is selected from polyoxyethylene alkyl ethers, polyoxyethylene polyoxypropylene alkyl ethers, or a mixture thereof. Typically, total HLB (hydrophilic-lipophilic balance) of the nonionic surfactant that is used is in the range of about 8-16, more typically in the range of 10-15.

Other non-limiting examples of nonionic surfactants useful herein include alkoxylated fatty alcohols, e.g., ethoxylated nonionic surfactant, and amine oxide surfactants. These materials are described in U.S. Pat. No. 4,285,841, Barrat et al, issued Aug. 25, 1981. The nonionic surfactant may be selected from the ethoxylated alcohols and ethoxylated alkyl phenols of the formula $R(OC_2H_4)_nOH$, wherein R is selected from the group consisting of aliphatic hydrocarbon radicals containing from about 8 to about 15 carbon atoms and alkyl phenyl radicals in which the alkyl groups contain from about 8 to about 12 carbon atoms, and the average value of n is from about 5 to about 15. These surfactants are more fully described in U.S. Pat. No. 4,284,532, Leikhim et al, issued Aug. 18, 1981. Further non-limiting examples of nonionic surfactants useful herein include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1 to 30, as discussed in U.S. Pat. No. 6,153,577, U.S. Pat. No. 6,020,303 and U.S. Pat. No. 6,093,856; Alkylpolysaccharides as discussed in U.S. Pat. No. 4,565,647 to Llenado, issued Jan. 26, 1986; specifically alkylpolyglycosides as discussed in U.S. Pat. No. 4,483,780 and U.S. Pat. No. 4,483,779; Polyhydroxy fatty acid amides as discussed in U.S. Pat. No. 5,332,528, WO 92/06162, WO 93/19146, WO 93/19038, and WO 94/09099; and ether capped poly(oxyalkylated) alcohol surfactants as discussed in U.S. Pat. No. 6,482,994 and WO 01/42408.

Cationic Surfactants

Cationic surfactants include, for example, alkyl trimethylammonium chloride, alkylamine hydrochloric acid salts, alkylamine acetate, alkylbenzene dimethyl ammonium chloride and the like.

Non-limiting examples of cationic surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, specifically amido propyldimethyl amine (APA).

Anionic Surfactants

Suitable anionic surfactants include sulphate and sulphonate surfactants. Suitable sulphonate surfactants include alkyl benzene sulphonate, in one aspect, $C_{10-13}$ alkyl benzene sulphonate. Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic surfactant is alkyl benzene sulphonate that is obtained by DETAL catalyzed process, although other synthesis routes, such as HF, may also be suitable. In one aspect a magnesium salt of LAS is used.

Suitable sulphate surfactants include alkyl sulphate, in one aspect, $C_{8-18}$ alkyl sulphate, or predominantly $C_{12}$ alkyl sulphate.

Another suitable sulphate surfactant is alkyl alkoxylated sulphate, in one aspect, alkyl ethoxylated sulphate, in one aspect, a $C_{8-18}$ alkyl alkoxylated sulphate, in another aspect, a $C_{8-18}$ alkyl ethoxylated sulphate, typically the alkyl alkoxylated sulphate has an average degree of alkoxylation of from 0.5 to 20, or from 0.5 to 10, typically the alkyl alkoxylated sulphate is a $C_{8-18}$ alkyl ethoxylated sulphate having an average degree of ethoxylation of from 0.5 to 10, from 0.5 to 7, from 0.5 to 5 or even from 0.5 to 3.

The alkyl sulphate, alkyl alkoxylated sulphate, and alkyl benzene sulphonates may be linear or branched, substituted or un-substituted.

The surfactant may be a mid-chain branched surfactant, in one aspect, a mid-chain branched anionic detersive surfactant, in one aspect, a mid-chain branched alkyl sulphate and/or a mid-chain branched alkyl benzene sulphonate, for example a mid-chain branched alkyl sulphate. In one aspect, the mid-chain branches are $C_{1-4}$ alkyl groups, typically methyl and/or ethyl groups.

Zwitterionic Surfactants

Examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides. and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$.

Ampholytic Surfactants

Specific, non-limiting examples of ampholytic surfactants include: aliphatic derivatives of secondary or tertiary amines, or aliphatic derivatives of heterocyclic secondary and tertiary amines in which the aliphatic radical can be straight- or branched-chain. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of ampholytic surfactants.

Amphoteric Surfactants

Amphoteric surfactants include, for example, N-acylamidopropyl-N,N-dimethyl ammonia betaines, N-acylamidopropyl-N,N'-dimethyl-N'-β-hydroxypropyl ammonia betaines, and the like.

Examples of amphoteric surfactants include: aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. Examples of compounds falling within this definition are sodium 3-(dodecylamino)propionate, sodium 3-(dodecylamino) propane-1-sulfonate, sodium 2-(dodecylamino) ethyl sulfate, sodium 2-(dimethylamino) octadecanoate, disodium 3-(N-carboxymethyldodecylamino)propane 1-sulfonate, disodium octadecyl-imminodiacetate, sodium 1-carboxymethyl-2-undecylimidazole, and sodium N,N-bis(2-hydroxyethyl)-2-sulfato-3-dodecoxypropylamine. See U.S. Pat. No. 3,929,678 to Laughlin et al., issued Dec. 30, 1975 at column 19, lines 18-35, for examples of amphoteric surfactants.

Other Surfactants

Polyester modified silicone or other silicone surfactants may also be optionally used in small amounts, e.g., less than 5%.

Water

The amino silicone nanoemulsion comprises from about 10% to about 99.99%, of water, by weight. In some aspects, such as a raw material sourced in manufacturing, the amino silicone nanoemulsion may include water in amounts of from about 10% to about 50%, by weight. In some aspects, such as a concentrated consumer product such as a laundry detergent or a shampoo, the amino silicone nanoemulsion may include water in amounts of from about 20% to about 90%, by weight. In some aspects, such as a diluted consumer product being used as a treatment composition, the amino silicone nanoemulsion may include water in amounts of from about 20% to about 99.99%, by weight.

Protonating Agent

The protonating agent is generally a monoprotic or multiprotic, water-soluble or water-insoluble, organic or inorganic acid. Suitable protonating agents include, for example, formic acid, acetic acid, propionic acid, malonic acid, citric acid, hydrochloric acid, sulfuric acid, phosphoric acid, nitric acid, or a mixture thereof. In some aspects, the protonating agent is selected from formic acid, acetic acid, or a mixture thereof. In some aspects, the protonating agent is acetic acid. Generally, the acid is added in the form of an acidic aqueous solution. The protonating agent is added in an amount necessary to achieve a nanoemulsion pH of from about 3.5 to about 7.0. In certain aspects, the amino silicone nanoemulsions comprise the protonating agent in an amount necessary to achieve a pH of from about 3.5 to about 6.5 or about 4.0 to about 6.0. In other aspects, the amino silicone nanoemulsions comprise the protonating agent in an amount necessary to achieve a pH of from about 5.0 to about 6.0 or about 5.5.

Stabilizer

The amino silicone nanoemulsions may also comprise auxiliary stabilizers selected from mono- or polyalcohols and ethers thereof, which have a boiling point or boiling range of at most 260° C. at 0.10 MPa. Examples of monoalcohols are ethanol, n-propanol, isopropanol and butanol. Examples of polyalcohols are ethylene glycol and propylene glycol. Examples of polyalcohol ethers are ethylene glycol monobutyl ether, ethylene glycol monoethyl ether and diethylene glycol monoethyl ether. If used, the nanoemulsions may include auxiliary stabilizers at levels up to about 10%. Certain embodiments of the nanoemulsions optionally comprise from about 1% to about 7%, while others optionally comprise from about 2% to about 5% of the auxiliary stabilizer.

Optional Nanoemulsion Adjunct Ingredients

The amino silicone nanoemulsions may additionally include further substances, such as preservatives, scents, corrosion inhibitors and dyes. Examples of preservatives are alcohols, formaldehyde, parabens, benzyl alcohol, propionic acid and salts thereof and also isothiazolinones. The nanoemulsions may further include yet other additives, such as non-silicon-containing oils and waxes. Examples thereof are rapeseed oil, olive oil, mineral oil, paraffin oil or non-silicon-containing waxes, for example carnauba wax and candelilla wax or montan acid and montan ester waxes, incipiently oxidized synthetic paraffins, polyethylene waxes, polyvinyl ether waxes and metal-soap-containing waxes. In some aspects, the amino silicone nanoemulsions further comprise carnauba wax, paraffin wax, polyethylene wax, or a mixture thereof. The nanoemulsions may comprise up to about 5% by weight of the nanoemulsion or from about 0.05% to about 2.5% by weight of the nanoemulsion of such further substances.

Method of Making

The amino silicone nanoemulsions of the present disclosure may be prepared by mixing abovementioned the amino silicone fluid compound and the solvent. More specifically, the method for preparing the amino silicone nanoemulsion of the invention includes the steps of: mixing the amino silicone fluid with a reduced concentration of solvent, e.g., from about 0.5% to about 5% by weight of the amino silicone fluid compound, at a low speed, e.g., less than 500 rpm, for 30 minutes; curing the mixture of amino silicone and solvent at a low degree, e.g., for less than 24 hours at room temperature or for less than 20 minutes at 100° C.); adding a reduced concentration of surfactant, e.g., from about 1% to about 30% by weight of the amino silicone compound, water, and a protonating agent to the mixture of amino silicone and solvent and mixing the combined mixture at low speed, e.g., less than 500 rpm for 30 minutes. Optional adjunct materials are then added to the mixture and mixed appropriately for another 30 minutes.

Treatment Composition

The amino silicone nanoemulsions of the present invention may be incorporated into treatment compositions or cleaning compositions, such as, but not limited to, a fabric care composition, a dish cleaning composition, a home care composition, a beauty care composition, or a personal care composition. In some aspects, the treatment composition comprises from about 0.001% to about 99% by weight of the composition, of the amino silicone nanoemulsion. In certain aspects, the treatment composition comprises from about 0.001% to about 15% of the amino silicone nanoemulsion, by weight of the composition.

Examples of treatment and cleaning compositions include, but are not limited to, liquid laundry detergents, solid laundry detergents, laundry soap products, laundry spray treatment products, laundry pre-treatment products, fabric enhancer products, hand dish washing detergents, automatic dishwashing detergents, a beauty care detergent, hard surface cleaning detergents (hard surfaces include exterior surfaces, such as vinyl siding, windows, and decks), carpet cleaning detergents, conditioners, a shampoo, shave preparation products, and a household cleaning detergent. Examples of fabric care compositions suitable for the present disclosure include, but are not limited to, liquid laundry detergents, heavy duty liquid laundry detergents, solid laundry detergents, laundry soap products, laundry spray treatment products, laundry pre-treatment products, laundry soak products, heavy duty liquid detergents, and rinse additives. Examples of suitable dish cleaning compositions include, but are not limited to, automatic dishwasher detergents, detergents for hand washing of dishes, liquid dish soap, and solid granular dish soap. Examples of suitable home care compositions include, but are not limited to, rug or carpet cleaning compositions, hard surface cleaning detergents, floor cleaning compositions, window cleaning compositions, household cleaning detergents, and car washing detergents. Examples of suitable personal care compositions include, but are not limited to, beauty care cleansers, such as hair and skin cleansers, beauty bars, bar soap, bath beads, bath soaps, hand washing compositions, body washes and soaps, shampoo, conditioners, cosmetics, hair removal compositions, and oral care compositions.

In some aspects, the treatment composition may be provided in combination with a nonwoven substrate, as a treatment implement.

In certain aspects, the compositions provide water and/or oil repellency to the treated surface, thereby reducing the propensity of the treated surface to become stained by deposited water- or oil-based soils.

By "surfaces" it is meant any surface. These surfaces may include porous or non-porous, absorptive or non-absorptive substrates. Surfaces may include, but are not limited to, celluloses, paper, natural and/or synthetic textiles fibers and fabrics, imitation leather and leather, hair and skin. Selected aspects of the present invention are applied to natural and/or synthetic textile fibers and fabrics.

By "treating a surface" it is meant the application of the composition onto the surface. The application may be performed directly, such as spraying or wiping the composition onto a hard surface. The composition may or may not be rinsed off, depending on the desired benefit.

The present invention also encompasses the treatment of a fabric as the surface. This can be done either in a "pretreatment mode", where the composition is applied neat onto the fabric before the fabrics are washed or rinsed, or a "post-treatment mode", where the composition is applied neat onto the fabric after the fabric is washed or rinsed. The treatment may be performed in a "soaking mode", where the fabric is immersed and soaked in a bath of neat or diluted composition. The treatment may also be performed in a "through the wash" or "through the rinse" mode where the treatment composition, as defined herein, is added to the wash cycle or the rinse cycle of a typical laundry wash machine cycle. When used in the wash or rinse cycle, the compositions are typically used in a diluted form. By "diluted form" it is meant that the compositions may be diluted in the use, preferably with water at a ratio of water to composition up to 500:1, or from 5:1 to 200:1, or from 10:1 to 80:1.

Such treatment compositions may comprise carriers, which may be any known material that is useful in delivering the treatment compositions to the surface to be treated. The carrier may be as simple as a single component delivery vehicle, such as water or alcohol, which would allow the nanoemulsion to be sprayed onto a surface. Alternatively, the carrier may be complex, such as a cleaning composition, e.g., a laundry detergent where the nanoemulsion would be applied in conjunction with the other beneficial uses of the complex carrier.

Such treatment compositions may comprise various other materials, including bleaching agents, bleach activators, detersive surfactants, builders, chelating agents, smectite clays, dye transfer inhibiting agents, dispersants, enzymes, and enzyme stabilizers, catalytic metal complexes, polymeric dispersing agents, clay and soil removal/anti-redeposition agents, brighteners, suds suppressors, suds boosters, dyes, additional perfumes and perfume delivery systems, structure elasticizing agents, fabric softeners, carriers, hydrotropes, processing aids and/or pigments.

Detersive Surfactants—The treatment compositions according to the present disclosure may comprise a detersive surfactant or detersive surfactant system. Suitable detersive surfactants include nonionic surfactant, anionic surfactant, cationic surfactant, ampholytic surfactant, zwitterionic surfactant, semi-polar nonionic surfactant, or a mixture thereof. The detersive surfactant is typically present at a level of from about 0.1%, from about 1%, or even from about 5%, by weight of the treatment composition, to about 99.9%, to about 80%, to about 35%, or even to about 30%, by weight of the treatment composition. The specific surfactants described above, in the context of the nanoemulsion itself, may be included in the treatment compositions as detersive surfactants. When included in the treatment compositions (as opposed to the nanoemulsion itself), these surfactants are generally included at appropriate concentrations such that the surfactants provide a detersive or cleaning benefit.

Builders—The treatment compositions of the present disclosure may comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The treatment compositions may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The treatment compositions of the present disclosure may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole (PVPVI), polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The treatment compositions of the present disclosure may also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The treatment compositions may comprise one or more detergent enzymes, which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in the treatment compositions, e.g., detergents, may be stabilized by various techniques. The enzymes employed herein can be stabilized by the presence of water-soluble sources of calcium and/or magnesium ions in the finished compositions that provide such ions to the enzymes.

In some aspects, the treatment composition comprises an amino silicone nanoemulsion and a carrier. Typically, the amino silicone nanoemulsion is substantially free of a silicone resin. In some aspects, the treatment composition comprises an amino silicone nanoemulsion, a carrier, and a perfume, a detersive surfactant system, or a cleaning adjunct additive. The detersive surfactant system may comprise one or more surfactants selected from nonionic surfactants, cationic surfactants, anionic surfactants, zwitterionic surfactants, ampholytic surfactants, or amphoteric surfactants. In some aspects, the detersive surfactant system comprises a surfactant selected from $C_{10}$-$C_{16}$ alkyl benzene sulfonates, $C_8$-$C_{18}$ alkyl sulfate, $C_8$-$C_{18}$ alkyl ethoxylated sulfate, or a mixture thereof.

In certain aspects of the present disclosure, the treatment composition is a fabric care composition. Such a fabric care composition may take the form of detergent composition or a rinse added fabric conditioning compositions. Such compositions may comprise a fabric softening active and a dispersant polymer, to provide a stain repellency benefit to fabrics treated by the composition, typically from about 0.00001 wt. % (0.1 ppm) to about 1 wt. % (10,000 ppm), or even from about 0.0003 wt. % (3 ppm) to about 0.03 wt. % (300 ppm) based on total rinse added fabric conditioning composition weight. In another specific aspect, the compositions are rinse added fabric conditioning compositions. Examples of typical rinse added conditioning composition can be found in U.S. Provisional Patent Application Ser. No. 60/687,582 filed on Oct. 8, 2004.

In some aspects, the treatment composition is encapsulated in a water-soluble or water-dispersible pouch. The water-soluble film or pouch may comprise polyvinyl alcohol, polyvinyl acetate, or mixtures thereof. In some aspects, the unit dose form comprises at least two compartments, or at least three compartments. At least one compartment may be superimposed on another compartment.

In certain aspects, the treatment composition may be in the form of a granule. Granular treatment compositions may include any number of conventional detergent ingredients, such as the components described above, e.g., surfactants, chelants, enzymes. Granular detergent compositions typically comprise from about 1% to 95% by weight of a surfactant. Granular detergents can be made by a wide variety of processes, non-limiting examples of which include spray drying, agglomeration, fluid bed granulation, marumarisation, extrusion, or a combination thereof. Bulk densities of granular detergents generally range from about 300 g/1-1000 g/l. The average particle size distribution of granular detergents generally ranges from about 250 microns-1400 microns.

In certain aspects of the present disclosure, the treatment composition disclosed herein is selected from a beauty care composition, a hand washing composition, a body wash composition, a shampoo composition, a conditioner composition, a cosmetic composition, a hair removal composition, a oral care composition, a laundry spray composition, a laundry rinse additive composition, a liquid laundry detergent compositions, a solid laundry detergent compositions, a hard surface cleaning compositions, a liquid hand dishwashing compositions, a solid automatic dishwashing compositions, a liquid automatic dishwashing, and a tab/unit dose form automatic dishwashing compositions, and a laundry detergent compositions contained in a water-soluble pouch.

Method of Making Treatment Composition Comprising Amino Silicone Nanoemulsion

The treatment compositions disclosed herein may be prepared by combining the components thereof in any convenient order and by mixing, e.g., agitating, the resulting component combination to form a phase stable cleaning composition. In one aspect, a liquid matrix is formed containing at least a major proportion, or even substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactant and the solid ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills are incorporated. As a variation of the composition preparation procedure described above, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

In another aspect of producing liquid cleaning compositions, the amino silicone nanoemulsion may first be combined with one or more liquid components to form an aqueous amino silicone nanoemulsion premix, and this aqueous amino silicone nanoemulsion premix is added to a composition formulation containing a substantial portion, for example more than 50% by weight, more than 70% by weight, or even more than 90% by weight, of the balance of components of the cleaning composition. For example, in the methodology described above, both the aqueous amino silicone nanoemulsion premix and the enzyme component are added at a final stage of component additions. In another aspect, the aqueous amino silicone nanoemulsion is encapsulated prior to addition to the detergent composition, the encapsulated aqueous amino silicone nanoemulsion is suspended in a structured liquid, and the suspension is added to a composition formulation containing a substantial portion of the balance of components of the cleaning composition.

Methods of Using Treatment Compositions

The treatment compositions of the present disclosure may be used in a method of treating a surface. The method of treating a surface comprises the step of applying the amino silicone nanoemulsion treatment composition of the present disclosure to a surface, where the surface is selected from fabric, skin, hair, or a hard surface.

Fabric Treatment

The treatment compositions disclosed in the present specification may be used to clean or treat a fabric, such as those described herein. Typically at least a portion of the fabric is contacted with an embodiment of the aforementioned fabric care compositions, in neat form or diluted in a liquor, for example, a wash liquor and then the fabric may be optionally washed and/or rinsed and/or dried without further treatment. In one aspect, a fabric is optionally washed and/or rinsed, contacted with an embodiment of the aforementioned fabric care compositions and then optionally washed and/or rinsed. For purposes of the present disclosure, washing includes but is not limited to, scrubbing, and mechanical agitation. The fabric may comprise most any fabric capable of being laundered or treated.

The fabric care compositions disclosed in the present specification can be used to form aqueous washing or treatment solutions for use in the laundering and/or treatment of fabrics. Generally, an effective amount of such compositions is added to water, preferably in a conventional fabric laundering automatic washing machine, to form such aqueous laundering solutions. The aqueous washing solution so formed is then contacted, preferably under agitation, with the fabrics to be laundered therewith. An effective amount of the fabric care composition, such as the liquid detergent compositions disclosed in the present specification, may be added to water to form aqueous laundering solutions that may comprise from about 500 to about 7,000 ppm or even from about 1,000 to about 3,000 ppm of fabric care composition.

In one aspect, the fabric care compositions may be employed as a laundry additive, a pre-treatment composition and/or a post-treatment composition.

Without being bound by theory it is believed the treatment of a fabric with compositions disclosed in the present specification may increase the time-to-wick of the fabric. Table 1 shows an increase in the time-to-wick of cotton fabric as a result of treatment with examples of compositions disclosed in the present specification.

In some aspects, there is provided a method of treating a surface comprising the step of applying the amino silicone nanoemulsion treatment composition of the present disclosure to a surface, where the surface is a fabric and where the water repellency relative to the untreated fabric is increased, as measured by an increase in Time to Wick. In certain aspects, the increase in Time to Wick is greater than about 100 seconds, or greater than about 500 seconds, or greater than about 1200 seconds. In some aspects, the oil repellency relative to the untreated fabric is increased, as measured by an increase in Time to Wick. In some aspects, the oil repellency relative to the untreated fabric is increased, as measured by an increase in Time to Wick greater than about 10 seconds.

Hair Treatment

The treatment compositions disclosed in the present specification may be used to clean or treat hair. Typically at least a portion of the hair is contacted with an embodiment of the aforementioned hair care compositions, in neat form or diluted in a liquor, for example, a wash liquor, and then the hair may be optionally washed and/or rinsed and/or dried without further treatment. In one aspect, hair is optionally washed and/or rinsed, contacted with an embodiment of the aforementioned hair care compositions and then optionally washed and/or rinsed and/or dried without further treatment. For purposes of the present disclosure, washing includes but is not limited to, scrubbing, and mechanical agitation.

The hair care compositions disclosed in the present specification can be used to form aqueous washing or treatment solutions for use in the washing and/or treatment of hair. Generally, an effective amount of such compositions is added to water to form such aqueous washing and/or treatment solutions. The aqueous washing and/or treatment solution so formed is then contacted with the hair to be washed or treated therewith.

Without being bound by theory, it is believed the treatment of the hair with compositions disclosed in the present specification may decrease the dry-time of the hair after treatment. For example if the treatment were a hair-conditioning treatment applied in the shower, the time required for the hair to dry after such treatment would be reduced by virtue of the treatment, relative to the time required for the hair to dry if there had been no such treatment. Table 2 shows a decrease in the dry-time of hair as a result of treatment with examples of compositions disclosed in the present specification.

In some aspects, there is provided a method of treating a surface comprising the step of applying the amino silicone nanoemulsion treatment composition of the present disclosure to a surface, where the surface is hair or skin and where the dry time relative to the untreated hair or skin is decreased, as measured by an decrease in Technical Dry Time. In some aspects, the Technical Dry Time is less than about 3 seconds.

Hard Surfaces

The treatment compositions disclosed in the present specification may be used to clean or treat hard surfaces, such as those described herein. Typically at least a portion of the hard surface is contacted with an embodiment of the aforementioned hard surface care compositions, in neat form or diluted in a liquor, for example, a wash liquor and then the hard surface may be optionally washed and/or rinsed and/or dried without further treatment. In one aspect, a hard surface is optionally washed and/or rinsed, contacted with an embodiment of the aforementioned hard surface care compositions and then optionally washed and/or rinsed and/or dried without further treatment. For purposes of the present disclosure, washing includes but is not limited to, scrubbing, and mechanical agitation.

The hard surface care compositions disclosed in the present specification can be used to form aqueous washing or treatment solutions for use in the washing and/or treatment of hard surfaces. Generally, an effective amount of such compositions is added to water to form such aqueous washing and/or treatment solutions. The aqueous washing and/or treatment solution so formed is then contacted with the hard surface to be washed or treated therewith.

Without being bound by theory, it is believed the treatment of the hard surface with compositions disclosed in the present specification may increase the contact angle of water or water-based composition and/or oily substances on the hard surface. Without being bound by theory it is believed that increasing the contact angle of substances on a hard surface increases the ease of removing said substances from the surface. Table 3 shows an increase in the contact angle of a silica wafer as a result of treatment with examples of compositions disclosed in the present specification.

In some aspects, there is provided a method of treating a surface comprising the step of applying the amino silicone nanoemulsion treatment composition of the present disclosure to a surface, where the surface is a hard surface and where the contact angle relative to the untreated hard surface is increased. In some aspects, the contact angle is greater than about 36 degrees.

While various specific embodiments have been described in detail herein, the present disclosure is intended to cover various different combinations of the disclosed embodiments and is not limited to those specific embodiments described herein. The various embodiments of the present disclosure may be better understood, when read in conjunction with the following representative examples. The following representative examples are included for purposes of illustration and not limitation.

EXAMPLES

Nanoemulsion Preparations
1. Preparation of Amino Silicone Nanoemulsions

In a 6 oz jar, 17.0 g of amino silicon fluid (Mn=34527 g/mol, pendent group —$(CH_2)_3NH(CH_2)_2NH_2$ [corresponds to A], m/n=49, 71 mol % $SiMe_3$ end groups, 29 mol % SiOH/SiOMe end groups, obtainable from Shin-Etsu Silicones of America, Inc) are premixed with 0.8 g of Di-Ethylene Glycol monoHexyl Ether (DEGHE, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 78.5 g of De-Ionized (DI) water are added to the jar in two steps and mixed at 500 rpm at room temperature for total of 40 minutes. 0.29 ml of glacial acetic acid (obtainable from VWR International) are added to adjust pH to 5.5. About 100 g of a 17% amino silicone nanoemulsions are prepared. Nanoemulsions are almost clear and colorless, average particle size is 50 nm.

2. Preparation of Amino Silicone Nanoemulsions

In a 6 oz jar, 17.0 g of amino silicon fluid from example 1 are premixed with 0.8 g of Di-Ethylene Glycol monoButyl Ether (DEGBE, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 78.5 g of DI water are added to the jar in two steps and mixed at 500 rpm at room temperature for total of 40 minutes. 0.29 ml of glacial acetic acid (obtainable from VWR International) are added to adjust pH to about 5.5. About 100 g of a 17% amino silicone nanoemulsions are prepared. Nanoemulsions are almost clear and colorless, average particle size is 60 nm.

3. Preparation of Amino Silicone Nanoemulsions

In a 6 oz jar, 17.0 g of amino silicon fluid from example 1 are premixed with 0.8 g of Ethylene Glycol monoHexyl Ether (EGHE, obtainable from TCI America, Inc) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 78.5 g of DI water are added to the jar in two steps and mixed at 500 rpm at room temperature for total of 40 minutes. 0.29 ml of glacial acetic acid (obtainable from VWR International) are added to adjust pH to about 5.5. About 100 g of a 17% amino silicone nanoemulsions are prepared. Nanoemulsions are almost clear and colorless, average particle size is 60 nm.

4. Preparation of Amino Silicone Nanoemulsions

In a 6 oz jar, 17.0 g of amino silicon fluid from example 1 are premixed with 0.8 g of Ethylene Glycol monoButyl Ether (EGBE, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 78.5 g of DI water are added to the jar in two steps and mixed at 500 rpm at room temperature for total of 40 minutes. 0.29 ml of glacial acetic acid (obtainable from VWR International) are added to adjust pH to about 5.5. About 100 g of a 17% amino silicone nanoemulsions are prepared. Nanoemulsions are almost clear and colorless, average particle size is 70 nm.

5. Preparation of Amino Silicone Nanoemulsions

In a 6 oz jar, 17.0 g of amino silicon fluid from example 1 are premixed with 2 g of Di-Ethylene Glycol monoHexyl Ether (DEGHE, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 77.3 g of DI water are added to the jar in two steps and mixed at 500 rpm at room temperature for total of 40 minutes. 0.29 ml of glacial acetic acid (obtainable from VWR International) are added to adjust pH to about 6. About 100 g of a 17% amino silicone nanoemulsions are prepared. Nanoemulsions are almost clear and colorless, average particle size is 35 nm.

6. Preparation of Amino Silicone Nanoemulsions

In a 6 oz jar, 17.0 g of amino silicon fluid from example 1 are premixed with 2 g of Ethylene Glycol monoHexyl Ether (EGHE, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 77.3 g of DI water are added to the jar in two steps and mixed at 500 rpm at room temperature for total of 40 minutes. 0.29 ml of glacial acetic acid (obtainable from VWR International) are added to adjust pH to about 5.5. About 100 g of a 17% amino silicone nanoemulsions are prepared. Nanoemulsions are almost clear and colorless, average particle size is 40 nm.

7. Preparation of Amino Silicone Nanoemulsions

In a 6 oz jar, 17.0 g of amino silicon fluid from example 1 are premixed with 2 g of 1,2-Hexane Diol (HD, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 77.3 g of DI water are added to the jar in two steps and mixed at 500 rpm at room temperature for total of 40 minutes. 0.29 ml of glacial acetic acid (obtainable from VWR International) are added to adjust pH to about 5.5. About 100 g of a 17% amino silicone nanoemulsions are prepared. Nanoemulsions are creamy, average particle size is 350 nm.

8. Preparation of Amino Silicone Nanoemulsions

In a 6 oz jar, 17.0 g of amino silicon fluid (Mn=37878 g/mol, pendent group —$(CH_2)_3NH(CH_2)_2NH_2$ [corresponds to A], m/n=125, 91 mol % $SiMe_3$ end groups, 9 mol % SiOH/SiOMe end groups, obtainable from Shin-Etsu Silicones of America, Inc) are premixed with 2 g of Di-Ethylene Glycol monoHexyl Ether (DEGHE, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 77.3 g of DI water are added to the jar in two steps and mixed at 500 rpm at room temperature for total of 40 minutes. 0.29 ml of glacial acetic acid (obtainable from VWR International) are added to adjust pH to about 6. About 100 g of a 17% amino silicone nanoemulsions are prepared. Nanoemulsions are milky, average particle size is 225 nm.

9. Preparation of Amino Silicone Nanoemulsions

In a 6 oz jar, 17.0 g of amino silicon fluid from example 1 are premixed with 0.8 g of Di-Ethylene Glycol monoHexyl Ether (DEGHE, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 78.5 g of DI water are added to the jar in two steps and mixed at 500 rpm at room temperature for total of 40 minutes. 1M hydrochloric acid (obtainable from VWR International) are added to adjust pH to about 5.5. About 100 g of a 17% amino silicone nanoemulsions are prepared. Nanoemulsions are almost clear and colorless, average particle size is 60 nm.

10. Preparation of Amino Silicone Nanoemulsions

In a 6 oz jar, 17.0 g of amino silicon fluid from example 1 are premixed with 0.4 g of Di-Ethylene Glycol monoHexyl Ether (DEGHE, obtainable from Sigma-Aldrich Chemie GmbH) and 0.4 g of Di-Ethylene Glycol monoButyl Ether (DEGBE, obtainable from Sigma-Aldrich Chemie GmbH) using IKA RW20 Digital Dual-Range Mixer at 500 rpm for 30 minutes in a 50° C. oil bath to obtain a clear, colorless solution. 1.4 g of Tergitol 15-s-5 and 2.0 g of Tergitol 15-s-12 (obtainable from Sigma-Aldrich Chemie GmbH) are added to the jar and mixed at 500 rpm at room temperature for 20 minutes. 78.5 g of DI water are added to the jar in two steps and mixed at 500 rpm at room temperature for total of 40 minutes. 0.29 ml of glacial acetic acid (obtainable from VWR International) are added to adjust pH to about 5.5. About 100 g of a 17% amino silicone nanoemulsions are prepared. Nanoemulsions are almost clear and colorless, average particle size is 70 nm.

Application Examples

Fabric Care Application Examples

The nanoemulsions of Examples 1-10 above are diluted to make treatment compositions in which the concentration of the amino silicone is either 100 ppm or 50 ppm, using DI water. Cotton fabric CW120 (obtainable from Empirical Manufacturing Company, Cincinnati, Ohio) is dipped in the solution and then dried at 60° C. for an hour in an oven. The Time to Wick (T2W) is measured on the fabrics according to the T2W testing method. Results are summarized in the Table below.

TABLE 1

| Nanoemulsions | | 1 | 2 | 3 | 4 | 5 | 6 | 7 | 8 | 9 | 10 |
|---|---|---|---|---|---|---|---|---|---|---|---|
| Amino Silicone (%) | m = 444, n = 9 | 100 | 100 | 100 | 100 | 100 | 100 | 100 | | 100 | 100 |
| | m = 500, n = 4 | | | | | | | | 100 | | |
| Solvent (%) | DEGHE | 4.7 | | | | 11.8 | | | 11.8 | 4.7 | 2.4 |
| | DEGBE | | 4.7 | | | | 11.8 | | | | 2.4 |
| | EGHE | | | 4.7 | | | | | | | |
| | EGBE | | | | 4.7 | | | | | | |
| | HD | | | | | | | 11.8 | | | |
| Surfactant (%) | Tergitol 15-S-12 | 8.2 | 8.2 | 8.2 | 8.2 | 8.2 | 8.2 | 8.2 | 8.2 | 8.2 | 8.2 |
| | Tergitol 15-S-5 | 11.8 | 11.8 | 11.8 | 11.8 | 11.8 | 11.8 | 11.8 | 11.8 | 11.8 | 11.8 |
| Protonating Agent to adjust pH | Acetic Acid | 5.5 | 5.5 | 5.5 | 5.5 | 5.5 | 5.5 | 5.5 | 5.5 | | 5.5 |
| | Hydrochloric Acid | | | | | | | | | 5.5 | |
| Water | | | | | To balance | | | | | | |
| Particle Size (nm) | | 50 | 60 | 60 | 70 | 35 | 40 | 350 | 225 | 60 | 70 |
| Water T2W (seconds) | 50 ppm amino silicone | 1270 | 2420 | | | 390 | 530 | 0 | 0 | 1400 | |
| | 100 ppm amino silicone | >3600 | >3600 | >3600 | >3600 | 3080 | 3200 | 0 | 0 | >3600 | >3600 |
| Oil T2W (seconds) | 100 ppm amino silicone | 36 | 36 | 36 | 36 | 17 | 16 | 10 | 11 | 36 | 36 |

Hair Care Application: Examples 11, 12, and 13 in Table 2 below are prepared following the nanoemulsion preparation procedure described in the Example 1 above. The nanoemulsions of Examples 11-13 are diluted to make treatment compositions in which the concentration of the aminosilicone is 10,000 ppm with DI water. Hair Switches (obtainable from International Hair Imports & Products, New York) are dipped in the solution and the drying time is measured on the hair switches according to the Hair Drying Time test method. Results are summarized in the Table 2 below.

TABLE 2

| | | Nanoemulsions | | | |
|---|---|---|---|---|---|
| | | 11 | 12 | 13 | 14 |
| Amino Silicone (%) | m = 221, n = 4 (m/n = 55) | 100 | | | Herbal Essences Drama Clean Shampoo (Lot# 11225395LF) |
| | m = 580, n = 10, (m/n = 58) | | 100 | | |
| | m = 195, n = 4, (m/n = 49) | | | 100 | |
| Solvent (%) | DEGHE | 4.7 | 4.7 | 4.7 | |
| Surfactant (%) | Tergitol 15-S-12 | 8.2 | 8.2 | 8.2 | |
| | Tergitol 15-S-5 | 11.8 | 11.8 | 11.8 | |
| Protonating Agent to adjust pH | Acetic Acid | 5.5 | 5.5 | 5.5 | |
| Water | | To Balance | | | |
| Particle Size (nm) | | 50 | 60 | 60 | |
| Drying Time (minutes) | 10,000 ppm Amino Silicone | 2.7 | 2.5 | 2.2 | 3.4 |

Hard Surface Application: Examples 15 and 16 in Table 3 below are prepared following the nanoemulsion preparation procedure described in the Example 1 above. The nanoemulsions of Examples 15-16 are diluted to make a treatment composition in which the concentration of the aminosilicone is 500 ppm, with DI water. Solutions are dropped on Silica Wafers (obtainable from Silicon Valley Microelectronic, Inc, CA) then dried at room temperature for 24 hours. Contact angles are measured on the silica wafers according to the contact angle test method.

TABLE 3

|  |  | Nanoemulsions | | |
|---|---|---|---|---|
|  |  | 15 | 16 | 17 |
| Amino Silicone (%) | m = 444, n = 9 | 100 |  | non |
|  | m = 500, n = 4 |  | 100 | Coated |
| Solvent (%) | DEGHE | 11.8 | 11.8 | Silica |
| Surfactant (%) | Tergitol 15-S-12 | 8.2 | 8.2 | Wafer |
|  | Tergitol 15-S-5 | 11.8 | 11.8 |  |
| Protonating Agent to adjust pH | Acetic Acid | 5.5 | 5.5 |  |
| Water |  | To Balance | | |
| Particle Size (nm) |  | 35 | 225 |  |
| Contact Angle (°) | 500 ppm AS | 93 | 79 | 36 |

Liquid laundry additive compositions 18-26 shown below have detailed percentages based on 100% active basis.

TABLE 4

| | Ingredient | | | | | | | | |
|---|---|---|---|---|---|---|---|---|---|
| | 18 | 19 | 20 | 21 | 22 | 23 | 24 | 25 | 26 |
| | | | | | Dosage | | | | |
| | 30 g | 30 g | 30 g | 30 g | 30 g | 30 g | 30 g | 30 g | 30 g |
| Nanoemulsions of Ex. 1-10 | 6.00% | 6.00% | 6.00% | 6.00% | 6.00% | 12.00% | 12.00% | 12.00% | 12.00% |
| cationic starch[1] | 1.20% | 1.20% | 1.20% | 1.20% | 1.20% | 1.20% | 1.20% | 1.20% | 1.20% |
| TAE80[2] | 0.25% | 0.25% | 0.25% | 0.25% | 0.25% | 0.25% | 0.25% | 0.25% | 0.25% |
| Antimicrobial | 0.02% | 0.02% | 0.02% | 0.02% | 0.02% | 0.02% | 0.02% | 0.02% | 0.02% |
| Perfume | 0.40% | 0.40% | 0.40% | 0.40% | 0.40% | 0.40% | 0.40% | 0.40% | 0.40% |
| Butyl Carbitol | 3.00% | 3.00% | 3.00% | 3.00% | 3.00% | 2.00% | 2.00% | 2.00% | 2.00% |
| Polyamine N-oxide | 0.00% | 0.83% | 1.67% | 3.34% | 5.00% | 0.00% | 1.67% | 3.34% | 5.00% |

[1] Akzo, EXP 5617-2301-28, available from Akzo Nobel.
[2] Tallow alkyl ethoxylated alcohol having an average degree of ethoxylation of 80.
3. Proxel GXL

Heavy Duty Liquid Detergent Compositions

Examples 27-31 are formulations for a heavy duty liquid (HDL) laundry detergent prepared using the amino silicone nanoemulsion according to aspects of the present disclosure. The amino silicone nanoemulsion is added to the formulations in an amount ranging from 0.001% to 15.0% by weight.

TABLE 5

| Ingredient | 27 | 28 | 29 | 30 | 31 |
|---|---|---|---|---|---|
| Sodium alkyl ether sulfate | 20.5 | 20.5 | 20.5 | | |
| C12-15 Alkyl Polyethoxylate (1.1) Sulfonic Acid | | | | 9.0 | |
| Branched alcohol sulfate | 5.8 | 5.8 | 5.8 | | |
| Linear alkylbenzene sulfonic acid | 2.5 | 2.5 | 2.5 | 1.0 | 8.0 |
| Alkyl ethoxylate | 0.8 | 0.8 | 0.8 | 1.5 | 6.0 |
| Amine oxide | 0 | 0.5 | 2 | | 1.0 |
| Citric acid | 3.5 | 3.5 | 3.5 | 2.0 | 2.5 |
| Fatty acid | 2.0 | 2.0 | 2.0 | | 5.5 |
| Protease | 0.7 | 0.7 | 0.7 | 0.4 | 0.4 |
| Amylase | 0.37 | 0.37 | 0.37 | 0.08 | 0.08 |
| Mannanase | | | | 0.03 | 0.03 |
| Borax (38%) | 3.0 | 3.0 | 3.0 | 1.0 | |
| MEA Borate | | | | | 1.5 |
| Calcium and sodium formate | 0.22 | 0.22 | 0.22 | 0.7 | |
| Amine ethoxylate polymers | 1.2 | 0.5 | 1.0 | 1.0 | 1.5 |
| Zwitterionic amine ethoxylate polymer | 1.0 | 2.0 | 1.0 | | |
| Nanoemulsions of Ex. 1-10 | 0.5 | 1.0 | 2.0 | 1.0 | 1.0 |
| DTPA[1] | 0.25 | 0.25 | 0.25 | 0.3 | 0.3 |
| Fluorescent whitening agent | 0.2 | 0.2 | 0.2 | | |
| Ethanol | 2.9 | 2.9 | 2.9 | 1.5 | 1.5 |
| Propylene Glycol | | | | 3.0 | 5.0 |
| Propanediol | 5.0 | 5.0 | 5.0 | | |
| Diethylene glycol | 2.56 | 2.56 | 2.56 | | |
| Polyethylene glycol 4000 | 0.11 | 0.11 | 0.11 | | |
| Monoethanolamine | 2.7 | 2.7 | 2.7 | 1.0 | 0.5 |
| Sodium hydroxide (50%) | 3.67 | 3.67 | 3.67 | 1.4 | 1.4 |
| Sodium cumene sulfonate | 0 | 0.5 | 1 | | 0.7 |
| Silicone suds suppressor | 0.01 | 0.01 | 0.01 | | 0.02 |
| Perfume | 0.5 | 0.5 | 0.5 | 0.30 | 0.3 |
| Dye | 0.01 | 0.01 | 0.01 | 0.016 | 0.016 |
| Opacifier[2] | 0.01 | 0.01 | 0.01 | | |
| Water | balance | balance | balance | balance | balance |
|  | 100.0% | 100.0% | 100.0% | 100.0% | 100.0% |

[1] Diethylenetriaminepentaacetic acid, sodium salt
[2] Acusol OP 301.

Granular Laundry Detergent Compositions

Examples 32-35 are formulations for a powder laundry detergent prepared using the amino silicone nanoemulsions according to the present disclosure. The amino silicone nanoemulsion is added to the formulations in an amount ranging from about 0.001% to about 15.0% by weight.

TABLE 6

| Ingredients | 32 | 33 | 34 | 35 |
|---|---|---|---|---|
| Nanoemulsions of Ex. 1-10 | 0.5 | 2.5 | 5.0 | 10 |
| Sodium alkylbenzenesulfonate | 16.0000 | 14.0000 | 12.0000 | 7.9 |
| Sodium alkyl alcohol ethoxylate (3) sulfate | — | — | — | 4.73 |
| Sodium mid-cut alkyl sulfate | | 1.5000 | 1.5000 | — |
| Alkyl dimethyl hydroxyethyl quaternary amine (chloride) | — | — | — | 0.5 |
| Alkyl ethoxylate | 1.3000 | 1.3000 | 1.3000 | — |

TABLE 6-continued

| Ingredients | 32 | 33 | 34 | 35 |
|---|---|---|---|---|
| Polyamine[1] | — | — | — | 0.79 |
| Nonionic Polymer[2] | 1.0000 | 1.0000 | 1.0000 | 1.0 |
| Carboxymethylcellulose | 0.2000 | 0.2000 | 0.2000 | 1.0 |
| Sodium polyacrylate | — | — | — | — |
| Sodium polyacrylate/maleate polymer | 0.7000 | 0.7000 | 0.7000 | 3.5 |
| Sodium tripolyphosphate | 10.0000 | 5.0000 | — | — |
| Zeolite | 16.0000 | 16.0000 | 16.0000 | — |
| Citric Acid | — | — | — | 5.0 |
| Sodium Carbonate | 12.5000 | 12.5000 | 12.5000 | 25.0 |
| Sodium Silicate | 4.0 | 4.0 | 4.0 | — |
| Enzymes[4] | 0.30 | 0.30 | 0.30 | 0.5 |
| Minors including moisture[5] | Balance | balance | balance | balance |

[1]Hexamethylenediamine ethoxylated to 24 units for each hydrogen atom bonded to a nitrogen, quaternized.
[2]Comb polymer of polyethylene glycol and polyvinylacetate
[3]Enzyme cocktail selected from known detergent enzymes including amylase, cellulase, protease, and lipase.
[4]Balance to 100% can, for example, include minors like optical brightener, perfume, suds suppresser, soil dispersant, soil release polymer, chelating agents, bleach additives and boosters, dye transfer inhibiting agents, aesthetic enhancers (example: Speckles), additional water, and fillers, including sulfate, $CaCO_3$, talc, silicates, etc.

Automatic Dishwasher Detergent Formulation

Examples 36-39 are automatic dishwasher powder formulations and example 40 is an automatic dishwasher gel formulation prepared using the amino silicone nanoemulsions according to the present disclosure. The amino silicone nanoemulsion is added to the formulations in an amount ranging from 0.001% to 15.0% by weight.

TABLE 7

| Ingredients | 36 | 37 | 38 | 39 | 40 |
|---|---|---|---|---|---|
| Polymer dispersant[1] | 0.5 | 5 | 6 | 5 | 3 |
| Carbonate | 35 | 40 | 40 | 35-40 | 0 |
| Sodium tripolyphosphate | 0 | 6 | 10 | 0-10 | 0-25 |
| Silicate solids | 6 | 6 | 6 | 6 | 0-10 |
| Bleach and Bleach activators | 4 | 4 | 4 | 4 | 2-6 |
| Enzymes | 0.3-0.6 | 0.3-0.6 | 0.3-0.6 | 0.3-0.6 | 0-1 |
| Disodium citrate dehydrate | 0 | 0 | 0 | 2-20 | 0 |
| Nonionic surfactant[2] | 0 | 0 | 0 | 0 | 0-2 |
| Nanoemulsions of Ex. 1-10 | 0.5 | 2 | 5 | 10 | 15 |
| Polygel DKP[4] | 0 | 0 | 0 | 0 | 1-2 |
| Hydrozincite | 0 | 0 | 0 | 0 | 0-0.3 |
| Zinc Sulfate | 0 | 0 | 0 | 0 | 0-0.8 |
| NaOH | 0 | 0 | 0 | 0 | 0-4 |
| KOH | 0 | 0 | 0 | 0 | 0-15 |
| Boric Acid | 0 | 0 | 0 | 0 | 0-4 |
| 1,2-propanediol | 0 | 0 | 0 | 0 | 0-1 |
| NaCl | 0 | 0 | 0 | 0 | 0-0.5 |
| Sodium Benzoate | 0 | 0 | 0 | 0 | 0.1-6 |
| Water, sulfate, perfume, dyes and other adjuncts | Balance to 100% | Balance to 100% | Balance to 100% | Balance to 100% | Balance to 100% |

[1]Anionic polymers such as Acusol, Alcosperse and other modified polyacrylic acid polymers.
[2]Such as SLF-18 polytergent from Olin Corporation
[3]Polyacrylate thickener from, e.g., 3V Co.

Liquid Dishwashing

Examples 41 and 42 are liquid hand dishwashing formulations prepared using the amino silicone nanoemulsions according to the present disclosure. The amino silicone nanoemulsion is added to the formulations in an amount ranging from 0.001% to 15.0% by weight.

TABLE 8

| Ingredients | 41 | 42 |
|---|---|---|
| $C_{12-13}$ Natural AE0.6S | 27.0 | 24.0 |
| $C_{10-14}$ mid-branched Amine Oxide | — | 6.0 |
| $C_{12-14}$ Linear Amine Oxide | 6.0 | — |
| SAFOL ® 23 Amine Oxide | 1.0 | 1.0 |
| $C_{11}E_9$ Nonionic[1] | 2.0 | 2.0 |
| Ethanol | 4.5 | 4.5 |
| Sodium cumene sulfonate | 1.6 | 1.6 |
| Polypropylene glycol 2000 | 0.8 | 0.8 |
| NaCl | 0.8 | 0.8 |
| 1,3 BAC Diamine[2] | 0.5 | 0.5 |
| Nanoemulsions of Examples 1-10 | 0.5 | 10 |
| Water | Balance | Balance |

[1]Nonionic may be either $C_{11}$ Alkyl ethoxylated surfactant containing 9 ethoxy groups.
[2]1,3, BAC is 1,3 bis(methylamine)-cyclohexane.

Laundry Unit Dose

Example 43 is a laundry unit dose formulation prepared using the amino silicone nanoemulsions according to the present disclosure. The amino silicone nanoemulsion is added to the formulations in an amount ranging from 0.001% to 15.0% by weight.

TABLE 9

| Ingredients | 43 |
|---|---|
| Glycerol (min 99) | 5.3 |
| 1,2-propanediol | 10.0 |
| Citric Acid | 0.5 |
| Monoethanolamine | 10.0 |
| Caustic soda | — |
| Dequest 2010 | 1.1 |
| Potassium sulfite | 0.2 |
| Nonionic Marlipal C24EO7 | 20.1 |
| HLAS | 24.6 |
| Optical brightener FWA49 | 0.2 |
| Nanoemulsions of Examples 1-10 | 0.5-15 |
| C12-15 Fatty acid | 16.4 |
| Polymer Lutensit Z96 | 2.9 |
| Polyethyleneimine ethoxylate PEI600 E20 | 1.1 |
| $MgCl_2$ | 0.2 |
| Enzymes | ppm |

Hard Surface Cleaning Compositions

Examples 44-52 are formulations for hard surface cleaning detergents prepared using the amino silicone nanoemulsion according to the present disclosure. The amino silicone nanoemulsion is added to the formulations in an amount ranging from 0.001% to 15.0% by weight.

TABLE 10

|  | 44 | 45 | 46 | 47 | 48 | 49 | 50 | 51 | 52 |
|---|---|---|---|---|---|---|---|---|---|
| Nanoemulsions of Examples 1-10 | 0.5 | 0.5 | 2.0 | 5.0 | 1.0 | 10.0 | 12.0 | 0.3 | 0.1 |
| Non ionic |  |  |  |  |  |  |  |  |  |
| C9/11 EO 8 | 6.0 | 6.0 | 7.0 |  |  | 6.0 | 6.0 | 6.0 | 6.2 |
| C9/11 EO 5 |  |  |  | 3.5 |  |  |  |  |  |

TABLE 10-continued

| | 44 | 45 | 46 | 47 | 48 | 49 | 50 | 51 | 52 |
|---|---|---|---|---|---|---|---|---|---|
| C12/14 EO21 | | | | 3.5 | | | | | |
| C11 EO 5 | | | | | 7.0 | | | | |
| Anionic | | | | | | | | | |
| NaLAS | 2.00 | 2.25 | 1.8 | | | | 1.80 | 2.25 | 1.80 |
| NAPS | | | | 3.1 | 3.0 | 3.0 | | | 3.1 |
| C12-14AS | | | | | | | | | |
| NaCS | | | | | | | | | |
| Co surfactants | | | | | | | | | |
| C12-14 AO | 1.50 | 1.25 | 1.50 | 3.9 | 2.0 | | 1.50 | 1.25 | 1.50 |
| C12-14 Betaine | | | | | 1.0 | 3.0 | | | |
| Quaternized Alkoxylated PEI | 0.1 | 0.3 | 0.5 | 0.1 | 0.2 | 0.2 | 0.4 | 0.05 | 0.3 |
| Thickeners | | | | | | | | | |
| HM-polyacrylate | 0.76 | 0.65 | 0.75 | | | | 0.70 | 0.65 | 0.65 |
| HM-HEC | | | | 0.6 | 0.8 | | | | |
| X gum | | | | | | 0.42 | | | |
| Buffer | | | | | | | | | |
| Na2CO3 | 0.77 | 0.4 | 0.75 | 0.1 | 0.3 | 0.2 | 0.75 | 0.4 | 0.75 |
| Citric Acid | 0.046 | 0.3 | 0.3 | 0.75 | 0.75 | 0.3 | 0.3 | 0.3 | 0.30 |
| Caustic | Up to 0.46 | Up to 0.76 | Up to 0.72 | Up to 0.5 | Up to 0.5 | Up to 0.3 | Up to 0.65 | Up to 0.65 | Up to 0.60 |
| Suds control | | | | | | | | | |
| Fatty Acid | 0.40 | 1.0 | 1.0 | 0.20 | 0.50 | 0.50 | 0.40 | 0.40 | 1.0 |
| Branched fatty alcohols | | | | | | | | | |
| Isofol 12 | | 0.2 | 0.1 | 0.2 | 0.3 | 0.5 | | | 0.1 |
| Isofol 16 | | | | | | | | | |
| Chelants | | | | | | | | | |
| DTPMP | | 0.3 | 0.30 | | | 0.2 | | | 0.3 |
| DTPA | 0.25 | | | | | | 0.25 | 0.25 | |
| GLDA | | | | | | | | | |
| Solvents | | | | | | | | | |
| IPA | | | | | | 2.0 | | | |
| n-BPPP | | | | | 2.0 | | | | |
| N-BP | | | | 4.0 | 2.0 | | | 2.0 | |
| Minors and Water | up to 100% | up to 100% | up to 100% | up to 100% | up to 100% | up to 100% | up to 100% | up to 100% | up to 100% |

$C_{9-11}$ $EO_5$ is a $C_{9-11}$ $EO_5$ nonionic surfactant commercially available from ICI or Shell. $C_{12,14}$ $EO_5$ is a $C_{12,14}$ $EO_5$ nonionic surfactant commercially available from Huls, A&W or Hoechst. $C_{11}$ $EO_5$ is a $C_{11}$ $EO_5$ nonionic surfactant. $C_{12,14}$ $EO_{21}$ is a $C_{12-14}$ $EO_{21}$ nonionic surfactant. NaPS is Sodium Paraffin sulphonate commercially available from Huls or Hoechst. NaLAS is Sodium Linear Alkylbenzene sulphonate commercially available from A&W. NaCS is Sodium Cumene sulphonate commercially available from A&W. Isalchem® AS is a $C_{12-13}$ sulphate surfactant commercially available from Sasol olefins and surfactants. $C_{12-14}$ AO is a $C_{12-14}$ amine oxide surfactant. $C_{12-14}$ Betaine is a $C_{12-14}$ betaine surfactant. DMPEG is a polyethyleneglycol dimethylether. HM-HEC is a cetylhydroxethylcellulose. Isofol 12® is 2-butyl octanol commercially available from Condea. Isofol 16® is 2-hexyl decanol commercially available from Condea. n-BP is normal butoxy propanol commercially available from Dow Chemicals. IPA is isopropanol. n-BPP is butoxy propoxy propanol available from Dow Chemicals.

Rinse-Off Personal Care Compositions

Examples 53-58 are formulations for rinse-off personal care compositions, which are multi-phase body wash compositions comprising a cleansing phase, e.g., phase containing surfactant, and a benefit phase, e.g., a phase containing moisturizer. These compositions may be easily modified to contain a single, cleansing phase (for example, a single-phase, water-based composition generally comprising water, surfactant, perfume, and colorant), instead of cleansing and benefit phases. The following rinse-off personal care compositions may also be easily modified to contain antiperspirant actives. Water-based antiperspirant and deodorant compositions (e.g., roll-ons) are also disclosed in U.S. Pat. No. 5,409,694. The amino silicone nanoemulsion (of examples 1-10) is added to the formulations in an amount ranging from 0.001% to 15.0% by weight.

TABLE 11

| Ingredient | 53 | 54 | 55 |
|---|---|---|---|
| Distilled Water | Q.S. | Q.S. | Q.S. |
| Nanoemulsions of Examples 1-10 | 0.001-15.0 | 0.001-15.0 | 0.001-15.0 |
| Sodium Tridecyl Ether Sulfate | 10.54 | 10.54 | 10.54 |
| Dehyton ML | 6.59 | 6.59 | 6.59 |
| Electrolyte | 4.01 | 4.01 | 4.01 |
| Iconol TDA3-Ethoxylated Tridecyl Alcohol | 0.84 | 0.84 | 0.84 |
| Cationic Polymer | 0.35 | 0.35 | 0.35 |
| Sodium Benzoate, NF | 0.24 | 0.24 | 0.24 |
| pH Adjustment Agent | 0.23 | 0.23 | 0.23 |
| Aqupec Ser W-300C | 0.17 | 0.17 | 0.17 |
| Dissovine na2-s | 0.13 | 0.13 | 0.13 |
| Kathon CG | 0.031 | 0.031 | 0.031 |

TABLE 11-continued

| Ingredient | 53 | 54 | 55 |
|---|---|---|---|
| Hydrogen peroxide solution, 20-40% | 0.004 | 0.004 | 0.004 |
| Soybean Oil | 15 | — | — |
| Petrolatume | — | 13 | 12.5 |
| Glyceryl monooleate | — | 2 | 2 |
| Mercaptopyridine-N-oxide (ZPT) | — | — | 0.5 |

TABLE 12

| Ingredient | 56 |
|---|---|
| Distilled Water | Q.S. |
| Nanoemulsions of Examples 1-10 | 0.001-15.0 |
| Sodium Laureth-1-Sulfate | 6.07 |
| Laurylamidopropyl Betaine (Amphosol LB) | 2.43 |
| Sodium Benzoate | 0.25 |
| EDTA (Dissolvine Na2S) | 0.1 |
| pH Adjustment Agent | 0.1 |
| Kathon CG | 0.0003 |
| Electrolyte | 1.25 |
| Castor Oil | 1 |
| AM:Triquat (95:5) (Polyquaternium-76) | 0.3 |
| Mercaptopyridine-N-oxide (ZPT) | 0.5 |

TABLE 13

| Ingredient | 57 | 58 |
|---|---|---|
| Water | Q.S. | Q.S. |
| Nanoemulsions of Examples 1-10 | 0.001-15.0 | 0.001-15.0 |
| Guar Hydroxy Propyl Trimonium Chloride | 0.2 | — |
| AM:TRIQUAT Copolymer | 0.2 | 0.2 |
| Sodium Laureth Sulfate, n = 1 | 10.5 | 6 |
| Sodium Lauryl Sulfate | — | 7 |
| Cocoamdopropyl Betaine | 1 | 1 |
| Ethylene Glycol Disterate | 2 | 2 |
| 330M silicone | 1.1 | — |
| Aminosilicone | — | 1.4 |
| Sodium Chloride | Up to 1.5% | Up to 1.5% |
| Fragrance | 0.75 | 0.75 |
| Preservatives, pH adjusters | Up to 1.3% | Up to 1.3% |
| Zinc Pyrithione | 1 | 1 |
| Zinc Hydroxy Carbonate | 1.61 | 1.61 |
| Petrolatum | 1 | 1 |
| Sodium Xylenesulfonate | Up to 1% | Up to 1% |

Hair Shampoo Compositions

Examples 59-63 are formulations for hair shampoos. The amino silicone nanoemulsion (of examples 1-10) is added to the formulations in an amount ranging from 0.001% to 15.0% by weight.

TABLE 14

| | All ingredients in % as added | | | | |
|---|---|---|---|---|---|
| Ingredient | 59 | 60 | 61 | 62 | 63 |
| Water | q.s. | q.s. | q.s. | q.s. | q.s. |
| Nanoemulsions of Examples 1-10 | 2 | 2 | 4 | 4 | 10 |
| Polyquaterium 76[1] | 0.25 | | | | 0.1 |
| Polquaterium 10[2] | | 0.25 | 0.25 | | |
| Polyquaterium 6[3] | | | | 0.1 | |
| Guar Hydroxypropyltrimonium Chloride[4] | | | | | 0.2 |
| Sodium Laureth Sulfate (SLE3S - 28% active)[5] | 21.43 | 35.71 | 35.71 | | |
| Sodium Laureth Sulfate (SLE1S - 29% active)[6] | | | | 44.83 | 37.93 |
| Sodium Lauryl Sulfate (SLS - 29% active)[7] | 12.07 | 24.14 | 24.14 | — | — |
| Coco monoethanolamide[8] | 1.0 | 0.5 | 0.5 | — | — |
| Cocoamdopropyl Betaine (30% active)[9] | 2.5 | — | — | 3.33 | 5.0 |
| Ethylene Glycol Disterate[10] | — | 1.5 | 1.5 | — | — |
| 330M silicone[11] | 1.43 | 1.43 | 1.43 | — | — |
| Silicone microemulsion[12] | — | — | — | — | 4 |
| Trihydroxystearn[13] | 0.25 | | 0.25 | 0.25 | 0.25 |
| Sodium Chloride[14] | Adjust as needed for viscosity | Adjust as needed for viscosity | Adjust as needed for viscosity | Adjust as needed for viscosity | Adjust as needed for viscosity |
| Fragrance | 0.7 | 0.7 | 0.7 | 0.7 | 0.7 |
| Preservatives, pH adjusters | Up to 1% | Up to 1% | Up to 1% | Up to 1% | Up to 1% |

[1]Acrylamide:Triquat cationic polymer, tradname: Mirapol AT from Rhodia,
[2]KG30M cationic cellulose polymer from Amerchol Dow
[3]Polydadmac, tradename: Mirapol 100S from Rhodia
[4]Jaguar C500 from Rhodia
[5]Sodium Laureth (3 molar ethylene oxide) Sulfate at 28% active, supplier: P&G
[6]Sodium Laureth (1 molar ethylene oxide) sulfate at 29% active, supplier: P&G
[7]Sodium Lauryl Sulfate at 29% active, supplier: P&G
[8]Coco monethanolamide at 85% active, supplier: Stephan Co
[9]Tegobetaine F-B, 30% active, supplier: Goldschmidt Chemical
[10]Ethylene Glycol Disterate at 100% active, supplier: Goldschmidt Chemical
[11]330M silicone, 100% active, supplier: Momentive (silicone used by P&G to make a 70% active, 30 um emulsion)
[12]Belsil 3560 VP silicone microemulsion from Wacker, 60,000 cst internal viscosity of silicone, approx. 125 nm
[13]Thixin R from Rheox Inc.
[14]Sodium Chloride USP (food grade) from Morton Hair Styling Product and Conditioning Compositions (Liquid Gel)

TABLE 15

| Ingredient | 64 |
| --- | --- |
| Nanoemulsions of Examples 1-10 | 2.00 g |
| Luviset ® Clear | 1.00 g |
| Surfactant 193 | 1.50 g |
| Carbomer | 0.30 g |
| AMP 95% | 0.30 g |
| Emulgin L | 0.20 g |
| Perfume | 0.15 g |
| Natrosol ® G | 0.40 g |
| Ethanol | 16.50 g |
| Water | Balance |

TABLE 16

| Liquid gel | |
| --- | --- |
| Ingredient | 65 |
| Nanoemulsions of Examples 1-10 | 3.00 g |
| Luviset ® Clear | 1.00 g |
| Vinylpyrrolidone/vinyl acetate copolymer | 1.00 g |
| Direct dye | 0.20 g |
| Surfactant 193 | 1.00 g |
| Xanthan Gum | 1.20 g |
| Citric acid | 0.10 g |
| Perfume | 0.15 g |
| Ethanol | 6.50 g |
| DMDM Hydantoin | 0.30 g |
| Water | Balance |

TABLE 17

| Liquid gel | |
| --- | --- |
| Ingredient | 66 |
| Nanoemulsions of Examples 1-10 | 4.00 g |
| Luviset ® Clear | 0.50 g |
| Glucose | 7.00 g |
| Direct dye | 0.50 g |
| Propylene glycol | 3.80 g |
| Hydroxypropylguar | 0.30 g |
| AMP 95% | 0.20 g |
| PEG-25 PABA | 0.50 g |
| PEG-40 Hydrogenated Castor Oil | 0.18 g |
| PPG-1-PEG-9 Lauryl Glycol Ether | 0.18 g |
| Perfume | 0.15 g |
| Ethanol | 16.50 g |
| Water | Balance |

TABLE 18

| Spray gel | |
| --- | --- |
| Ingredient | 67 |
| Nanoemulsions of Examples 1-10 | 1.00 g |
| Luviset ® Clear | 1.50 g |
| Luviskol ® VA 64 | 3.00 g |
| Ethanol | 18.00 g |
| Aminomethylpropanol 95% aqueous solution | 0.10 g |
| PEG-40 Hydrogenated Castor Oil | 0.20 g |
| Perfume | 0.20 g |
| Aculyn ® 48 | 0.50 g |
| Water | Balance |

The composition is packaged in a packaging with pump spray device.

TABLE 19

| Rapidly Drying Gel | |
| --- | --- |
| Ingredient | 68 |
| Nanoemulsions of Examples 1-10 | 1.00 g |
| Luviset ® Clear | 3.00 g |
| Aquaflex ® SF 40 | 2.80 g |
| Surfactant 193 | 1.50 g |
| Pemulen ® | 0.35 g |
| AMP 95% | 0.26 g |
| Methylmethoxycinnamate | 0.30 g |
| Perfume | 0.30 g |
| Ethanol | 34.20 g |
| Water | Balance |

TABLE 20

| Rapidly Drying Gel Spray | |
| --- | --- |
| Ingredient | 69 |
| Nanoemulsions of Examples 1-10 | 0.80 g |
| Luviset ® Clear | 1.00 g |
| Surfactant 193 | 1.00 g |
| Carbomer (Carbopol) | 0.23 g |
| AMP 95% | 0.22 g |
| Perfume | 0.15 g |
| Ethanol | 6.50 g |
| Water | Balance |

The composition is packaged in a packaging with pump spray device.

TABLE 21

| Blow-drying gel | |
| --- | --- |
| Ingredient | 70 |
| Nanoemulsions of Examples 1-10 | 1.80 g |
| Luviset ® Clear | 1.00 g |
| Surfactant 193 | 1.00 g |
| Hydroxypropylcellulose (Klucel ® HF) | 0.95 g |
| Citric acid | 0.10 g |
| Perfume | 0.15 g |
| Ethanol | 6.50 g |
| Water | Balance |

TABLE 22

| Rapid Drying Gel | |
| --- | --- |
| Ingredient | 71 |
| Nanoemulsions of Examples 1-10 | 2.90 g |
| Luviset ® Clear | 1.00 g |
| Polyvinylpyrrolidone K 90 | 1.80 g |
| Direct dye | 1.00 g |
| Surfactant 193 | 1.50 g |
| Synthalen ® W 2000 | 1.00 g |
| AMP 95% | 0.30 g |
| PEG-25 PABA (Uvinul ® P 25) | 0.30 g |
| Panthenol | 0.15 g |
| Perfume | 0.30 g |
| Ethanol | 34.20 g |
| Keratin hydrolysate | 0.10 g |
| Water | Balance |

TABLE 23

| Gel - strong hold | |
|---|---|
| Ingredient | 72 |
| Nanoemulsions of Examples 1-10 | 3.80 g |
| Luviset ® Clear | 1.00 g |
| VA/CROTONATES COPOLYMER (Luviset ® CA 66) | 2.50 g |
| Sorbitol | 4.20 g |
| Direct dye | 0.?? g |
| Carbomer (Tego Carbomer) | 0.80 g |
| AMP 95% | 0.30 g |
| Methylparaben | 0.20 g |
| PEG-40 Hydrogenated Castor Oil | 0.20 g |
| Panthenol | 0.10 g |
| Perfume | 0.20 g |
| Ethanol | 5.00 g |
| Water | Balance |

TABLE 24

| Gel - strong hold | |
|---|---|
| Ingredient | 73 |
| Nanoemulsions of Examples 1-10 | 5.80 g |
| Luviset ® Clear | 1.00 g |
| Aquaflex ® SF 40 | 1.50 g |
| Vinyl acetate/crotonic acid copolymer | 1.20 g |
| Sorbitol | 4.20 g |
| Structure ® 3001 | 0.12 g |
| AMP 95% | 0.35 g |
| PEG-25 PABA | 0.50 g |
| Dekaben ® LMB | 0.20 g |
| PEG-40 Hydrogenated Castor Oil | 0.20 g |
| Panthenol | 0.10 g |
| Perfume | 0.20 g |
| Ethanol | 5.00 g |
| Water | Balance |

TABLE 25

| Gel - normal hold | |
|---|---|
| Ingredient | 74 |
| Nanoemulsions of Examples 1-10 | 3.80 g |
| Luviset ® Clear | 1.50 g |
| Glycerol | 5.20 g |
| Propylene glycol | 4.00 g |
| Ammonium Acryloyldimethyltaurate/VP Copolymer (Aristoflex ® AVC) | 0.35 g |
| AMP 95% | 0.26 g |
| Polysorbate-40 | 1.00 g |
| Methylparaben | 0.20 g |
| PEG-25 PABA | 0.50 g |
| Perfume | 0.20 g |
| Ethanol | 4.50 g |
| Water | Balance |

TABLE 26

| Pump - setting foam | |
|---|---|
| Ingredient | 75 |
| Nanoemulsions of Examples 1-10 | 0.20 g |
| Luviset ® Clear | 1.30 g |
| Vinyl acetate/crotonic acid copolymer | 0.30 g |
| Cocamidopropyl Hydroxysultaine | 0.40 g |
| Citric acid | 0.10 g |
| Ethanol | 8.90 g |
| Betaine | 0.10 g |

TABLE 26-continued

| Pump - setting foam | |
|---|---|
| Ingredient | 75 |
| Perfume | 0.15 g |
| Water | Balance |

The composition is packaged in a packaging with mechanically operated pump foaming device.

TABLE 27

| Pump - setting foam | |
|---|---|
| Ingredient | 76 |
| Nanoemulsions of Examples 1-10 | 1.20 g |
| Luviset ® Clear | 1.50 g |
| Acrylic acid/ethyl acrylate/N-tert-butylacrylamide Copolymer | 0.40 g |
| Direct dye | 1.90 g |
| Cocamidopropyl Hydroxysultaine | 0.40 g |
| Citric acid | 0.10 g |
| Dekaben ® LMP | 0.20 g |
| Camomile blossom extract | 0.10 g |
| Perfume | 0.15 g |
| Water | Balance |

The composition is packaged in a packaging with mechanically operated pump foaming device.

TABLE 28

| Pump - setting foam | |
|---|---|
| Ingredient | 77 |
| Nanoemulsions of Examples 1-10 | 7.20 g |
| Luviset ® Clear | 1.20 g |
| Polyquaternium-6 | 0.35 g |
| Cocamidopropyl Hydroxysultaine | 0.40 g |
| Panthenol | 0.10 g |
| Ethanol | 8.90 g |
| Betaine | 0.10 g |
| Perfume | 0.15 g |
| Water | Balance |

The composition is packaged in a packaging with mechanically operated pump foaming device.

TABLE 29

| Pump - setting foam | |
|---|---|
| Ingredient | 78 |
| Nanoemulsions of Examples 1-10 | 1.20 g |
| Luviset ® Clear | 2.50 g |
| Direct dye | 3.00 g |
| Ethanol | 8.90 g |
| Cocamidopropyl Hydroxysultaine | 0.20 g |
| Cetyltrimethylammonium chloride | 0.20 g |
| Perfume | 0.15 g |
| Silk fibroin hydrolysate (Silkpro ®) | 0.10 g |
| Water | Balance |

The composition is packaged in a packaging with mechanically operated pump foaming device.

TABLE 30

| Pump - setting foam | |
|---|---|
| Ingredient | 79 |
| Nanoemulsions of Examples 1-10 | 2.20 g |
| Luviset ® Clear | 2.00 g |
| Celquat ® L200 | 0.30 g |
| Direct dye | 0.80 g |
| Ethanol | 8.90 g |
| Cocamidopropyl Hydroxysultaine | 0.20 g |
| Cetyltrimethylammonium chloride | 0.20 g |
| Perfume | 0.15 g |
| Citric acid | 0.10 g |
| Betaine | 0.10 g |
| Water | Balance |

The composition is packaged in a packaging with mechanically operated pump foaming device.

TABLE 31

| Pump - setting foam | |
|---|---|
| Ingredient | 80 |
| Nanoemulsions of Examples 1-10 | 1.20 g |
| Luviset ® Clear | 1.30 g |
| Polyquaternium-11 | 0.30 g |
| Direct dye | 0.20 g |
| Cocamidopropyl Hydroxysultaine | 0.40 g |
| Propylene glycol | 1.00 g |
| Methylparaben | 0.20 g |
| Perfume | 0.15 g |
| Water | Balance |

The composition is packaged in a packaging with mechanically operated pump foaming device.

TABLE 32

| Pump - setting foam | |
|---|---|
| Ingredient | 81 |
| Nanoemulsions of Examples 1-10 | 1.20 g |
| Luviset ® Clear | 1.80 g |
| Direct dye | 1.90 g |
| Cocamidopropyl Hydroxysultaine | 0.40 g |
| Rosemary leaf extract (Extrapon ® Rosemary) | 0.10 g |
| Ethanol | 8.90 g |
| Extrapon ® seven herbs - extract | 0.10 g |
| Panthenyl ethyl ether | 0.10 g |
| Perfume | 0.15 g |
| Water | Balance |

The composition is packaged in a packaging with mechanically operated pump foaming device.

TABLE 33

| Aerosol - setting foam - normal hold | |
|---|---|
| Ingredient | 82 |
| Nanoemulsions of Examples 1-10 | 4.20 g |
| Luviset ® Clear | 1.50 g |
| Butyl monoester of methyl vinyl ether/maleic acid copolymer | 0.50 g |
| Butane | 4.00 g |
| Propane | 4.00 g |
| Ethanol | 8.90 g |
| PEG-25 PABA | 0.40 g |
| Betaine | 0.15 g |
| Perfume | 0.15 g |
| Laureth-4 | 0.20 g |
| Cetrimonium bromide | 0.05 g |

TABLE 33-continued

| Aerosol - setting foam - normal hold | |
|---|---|
| Ingredient | 82 |
| Amodimethicone | 0.50 g |
| Water | Balance |

The composition is bottled in an aerosol can with foaming head.

TABLE 34

| Aerosol - setting foam - normal hold | |
|---|---|
| Ingredient | 83 |
| Nanoemulsions of Examples 1-10 | 5.20 g |
| Luviset ® Clear | 1.50 g |
| Polyquaternium-47 | 0.50 g |
| Butane | 4.00 g |
| Propane | 4.00 g |
| Betaine | 0.15 g |
| Dow Corning 1401 | 0.25 g |
| 2-Ethylhexyl 4-methoxycinnamate | 0.20 g |
| Perfume | 0.15 g |
| Laureth-4 | 0.20 g |
| Cetrimonium chloride | 0.07 g |
| Water | Balance |

The composition is bottled in an aerosol can with foaming head.

TABLE 35

| Aerosol - setting foam - extra strong hold | |
|---|---|
| Ingredient | 84 |
| Nanoemulsions of Examples 1-10 | 3.20 g |
| Luviset ® Clear | 2.10 g |
| Copolymer 845 | 2.50 g |
| Polyquaternium-4 | 1.00 g |
| Butane | 4.00 g |
| Propane | 4.00 g |
| Panthenol | 0.20 g |
| Perfume | 0.20 g |
| Abilquat ® 3270 | 0.70 g |
| Cetrimonium chloride | 0.07 g |
| Water | Balance |

The composition is bottled in an aerosol can with foaming head.

TABLE 36

| Aerosol - setting foam - extra strong hold | |
|---|---|
| Ingredient | 85 |
| Nanoemulsions of Examples 1-10 | 1.20 g |
| Luviset ® Clear | 2.10 g |
| Vinyl acetate/crotonic acid copolymer | 0.60 g |
| Polyquaternium-7 | 0.50 g |
| Butane | 4.00 g |
| Propane | 4.00 g |
| Ethanol 510 | 8.90 g |
| PEG-25 PABA | 0.40 g |
| Panthenol | 0.20 g |
| Perfume | 0.20 g |
| Laureth-4 | 0.20 g |
| C9-C11 Pareth-8 | 0.07 g |
| Water | Balance |

The composition is bottled in an aerosol can with foaming head.

TABLE 37

| Setting spray | |
|---|---|
| Ingredient | 85 |
| Nanoemulsions of Examples 1-10 | 0.20 g |
| Luviset ® Clear | 1.50 g |
| Aquaflex ® FX-64 | 1.00 g |
| Ethanol | 2.70 g |
| Polyquaternium-35 | 1.00 g |
| PEG-25 PABA | 0.70 g |
| Panthenol | 0.35 g |
| Perfume | 0.25 g |
| Cetrimonium chloride | 0.20 g |
| PEG-40 Hydrogenated Castor Oil | 0.21 g |
| Water | Balance |

The composition is bottled in a packaging with pump spray device.

TABLE 38

| Setting spray | |
|---|---|
| Ingredient | 86 |
| Nanoemulsions of Examples 1-10 | 1.20 g |
| Luviset ® Clear | 2.50 g |
| Octylacrylamide/Acrylates/Butylaminoethylmethacrylate Copolymer (Amphomer ®) | 2.00 g |
| Ethanol | 28.50 g |
| Aminomethylpropanol 95% | 0.60 g |
| Perfume | 0.25 g |
| Cetyltrimethylammonium bromide | 0.20 g |
| Water | Balance |

The composition is bottled in a packaging with pump spray device.

TABLE 39

| Setting spray | |
|---|---|
| Ingredient | 87 |
| Nanoemulsions of Examples 1-10 | 2.20 g |
| Luviset ® Clear | 1.00 g |
| Octylacrylamide/Acrylates/Butylaminoethylmethacrylate Copolymer (Amphomer ®) | 0.65 g |
| Celquat ® L200 | 0.20 g |
| Ethanol | 28.5 g |
| Aminomethylpropanol 95% | 0.60 g |
| Perfume | 0.25 g |
| Cetyltrimethylammonium chloride | 0.20 g |
| Water | Balance |

The composition is bottled in a packaging with pump spray device.

TABLE 40

| Non-aerosol blow-drying Lotion | |
|---|---|
| Ingredient | 88 |
| Nanoemulsions of Examples 1-10 | 3.50 g |
| Luviset ® Clear | 2.80 g |
| Vinyl Caprolactam/VP/Dimethylaminoethyl Methacrylate Copolymer (Advantage ® S) | 2.00 g |
| Ethanol | 28.50 g |
| Perfume | 0.25 g |
| Cetyltrimethylammonium chloride | 0.20 g |
| Water | Balance |

TABLE 41

| Nonaerosol blow-drying lotion | |
|---|---|
| Ingredient | 89 |
| Nanoemulsions of Examples 1-10 | 1.50 g |
| Luviset ® Clear | 3.10 g |
| Celquat ® L200 | 0.05 g |
| Diaformer ® Z-711 | 0.50 g |
| Ethanol | 27.00 g |
| Betaine | 0.10 g |
| Perfume | 0.25 g |
| PEG-40 Hydrogenated Castor Oil | 0.21 g |
| Cetyltrimethylammonium bromide | 0.20 g |
| Water | Balance |

TABLE 42

| Nonaerosol blow-drying Lotion | |
|---|---|
| Ingredient | 90 |
| Nanoemulsions of Examples 1-10 | 2.50 g |
| Luviset ® Clear | 3.00 g |
| Sodium polystyrenesulfonate (Flexan ®) | 2.30 g |
| Perfume | 0.20 g |
| Phenyltrimethicone (Baysilon ® oil PD 5) | 0.02 g |
| Water | 10.00 g |
| Ethanol | Balance |

The active ingredient solution is bottled in the ratio 45:55 with DME as propellant in an aerosol can.

TABLE 43

| VOC 80 Pump Spray - strong hold | |
|---|---|
| Ingredient | 91 |
| Nanoemulsions of Examples 1-10 | 1.50 g |
| Luviset ® Clear | 6.50 g |
| t-Butyl acrylate/Ethyl acrylate/Methacrylic acid Copolymer (Luvimer ® 100 P) | 0.50 g |
| Perfume | 0.20 g |
| AMP | 0.10 g |
| Betaine | 0.05 g |
| Ethanol | 55.00 g |
| Demineralized water | Balance |

The composition is bottled in a packaging with pump spray device.

TABLE 44

| Aerosol - hairspray | |
|---|---|
| Ingredient | 92 |
| Nanoemulsions of Examples 1-10 | 2.80 g |
| Octylacrylamide/Acrylic acid/Butylaminoethyl methacrylate/Methyl methacrylate/hydroxypropyl methacrylate Copolymer (Amphomer ®) | 3.00 g |
| Luviset ® Clear | 1.50 g |
| Phenyl trimethicone (Baysilon ® oil PD 5) | 0.02 g |
| Perfume | 0.20 g |
| Water | 10.00 g |
| AMP 95% | 0.48 g |
| Ethanol 510 | Balance |

The active ingredient solution is bottled in the ratio 45:55 with DME as propellant in an aerosol can.

TABLE 45

| Aerosol - hairspray | |
|---|---|
| Ingredient | 93 |
| Nanoemulsions of Examples 1-10 | 1.90 g |
| t-Butyl acrylate/Ethyl acrylate/Methacrylic acid Copolymer (Luvimer ® 100 P) | 3.30 g |
| Luviset ® Clear | 3.30 g |
| VA/CROTONATES COPOLYMER (Luviset ® CA 66) | 1.00 g |
| Perfume | 0.20 g |
| Water | 10.00 g |
| AMP 95% | 0.84 g |
| Ethanol | Balance |

The active ingredient solution is bottled in the ratio 45:55 with DME as propellant in an aerosol can.

TABLE 46

| Aerosol - hairspray | |
|---|---|
| Ingredient | 94 |
| Nanoemulsions of Examples 1-10 | 4.20 g |
| Luviset ® Clear | 2.50 g |
| t-Butyl acrylate/Ethyl acrylate/Methacrylic acid Copolymer (Luvimer ® 100 P) | 3.30 g |
| Aminomethylpropanol 95% | 0.85 g |
| Perfume | 0.20 g |
| Baysilon ® oil PD 5 | 0.02 g |
| Water | 10.00 g |
| Ethanol | Balance |

The active ingredient solution is bottled in the ratio 45:55 with DME as propellant in an aerosol can.

TABLE 47

| Volumizing aerosol foam | |
|---|---|
| Ingredient | 95 |
| Nanoemulsions of Examples 1-10 | 7.20 g |
| Luviset ® Clear | 1.90 g |
| Celquat ® L200 | 0.90 g |
| Aquaflex ® SF 40 | 0.40 g |
| Laureth-4 | 0.20 g |
| Cetrimonium chloride | 0.10 g |
| Perfume | 0.10 g |
| Butane | 2.20 g |
| Propane | 3.00 g |
| Isobutane | 0.80 g |
| Water | Balance |

The composition is bottled in an aerosol can with foaming head. Through use of the product on the hair, the hairstyle is given long-lasting volume.

TABLE 48

| Volumizing aerosol foam | |
|---|---|
| Ingredient | 96 |
| Nanoemulsions of Examples 1-10 | 8.00 g |
| Luviset ® Clear | 1.10 g |
| Chitosan | 1.00 g |
| Celquat ® L200 | 0.90 g |
| Aquaflex ® SF 40 | 0.40 g |
| Pyrrolidone carboxylic acid | 0.85 g |
| Laureth-4 | 0.20 g |
| Cetrimonium chloride | 0.10 g |
| Perfume | 0.10 g |
| Butane | 2.20 g |
| Propane | 3.00 g |
| Isobutane | 0.80 g |
| Water | Balance |

The composition is bottled in an aerosol can with foaming head. Through use of the product on the hair, the hairstyle is given long-lasting volume.

TABLE 49

| Volumizing aerosol foam | |
|---|---|
| Ingredient | 97 |
| Nanoemulsions of Examples 1-10 | 1.20 g |
| Luviset ® Clear | 2.00 g |
| Chitosan | 0.27 g |
| Celquat ® L200 | 1.00 g |
| Pyrrolidone carboxylic acid | 0.23 g |
| Direct dye | 0.90 g |
| Laureth-4 | 0.20 g |
| Cetrimonium chloride | 0.10 g |
| Perfume, preservative | 0.50 g |
| Water | Balance |

The composition is bottled with propane/butane 4.8 bar in the ratio of active ingredient solution:propellant gas=94:6 in an aerosol can with foaming head. Through use of the product on the hair, the hairstyle is given long-lasting volume.

TABLE 50

| Rinse out Conditioner | |
|---|---|
| Ingredient | 98 |
| Nanoemulsions of Examples 1-10 | 3.00 g |
| cetyltrimethyl ammonium chloride | 1.00 g |
| polymethylphenyl siloxane (CTFA: OUATERNIUM-80; Abil Quat ® 3272) | 1.00 g |
| phenoxy ethanol | 0.40 g |
| PHB-methylester | 0.20 g |
| Copolymer of aminoethyl aminopropyl siloxane and dimethyl siloxane emulsion as a mixture with polyethylenglycol ether of tridecyl alcohol and cetyl trimethyl ammoniumchloride (CTFA: AMODIMETHICONE & TRIDECETH-12 & CETRIMONIUM CHLORIDE; Dow Corning 949 Cationic Emulsion ®) | 1.00 g |
| Isododecane | 5.00 g |
| perfume oil | 0.40 g |
| Water | Balance |

TABLE 51

| Leave in Conditioner | |
|---|---|
| Ingredient | 99 |
| Nanoemulsions of Examples 1-10 | 1.00 g |
| 2-hydroxy-3-(trimethylamonio)propylether chloride guar gum | 0.50 g |
| sodium benzoate | 0.50 g |
| glyoxylic acid | 0.10 g |
| Creatine | 0.20 g |
| behenyl trimethylammonium chloride | 0.80 g |
| cetylstearyl alcohol | 0.60 g |
| stearic acid polyethylenglycol (20 EO) | 0.10 g |
| hydrolyzed silk | 0.10 g |

TABLE 51-continued

Leave in Conditioner

| Ingredient | 99 |
| --- | --- |
| perfume oil | 0.20 g |
| Water | Balance |

TABLE 52

Leave in Conditioner

| Ingredient | 100 |
| --- | --- |
| Nanoemulsions of Examples 1-10 | 1.80 g |
| vitamine E-acetate | 0.10 g |
| polymethylphenyl siloxane (CTFA: OUATERNIUM-80; Abil Quat(R) 3272) | 0.50 g |
| propylene glycol | 10.00 g |
| behenyl trimethylammonium chloride | 0.50 g |
| sodium chloride | 0.05 g |
| d-panthenol | 0.30 g |
| PHB-propylester | 0.30 g |
| Isododecane | 2.00 g |
| perfume oil | 0.20 g |
| Water | Balance |

TABLE 53

Split Ends Fluid

| Ingredient | 101 |
| --- | --- |
| Nanoemulsions of Examples 1-10 | 3.50 g |
| vitamine E-acetate | 0.10 g |
| polymethylphenyl siloxane (CTFA: OUATERNIUM-80; Abil Quat(R) 3272) | 0.50 g |
| cyclo penta siloxane (CTFA: CYCLOMETHICONE) | 21.00 g |
| dihydroxy polydimethyl siloxane (CTFA: DIMETHICONOL) | 2.50 g |
| Ethanol | 1.50 g |
| perfume oil | 0.60 g |
| Water | Balance |

TABLE 54

Styling lotion

| Ingredient | 102 |
| --- | --- |
| Luviskol VA64 | 1.00 g |
| Nanoemulsions of Examples 1-10 | 20.00 g |
| Eumulgin L | 0.20 g |
| Perfume | 0.15 g |
| PHENOXYETHANOL | 0.20 g |
| PHB-METHYLESTER | 0.12 g |
| DISODIUM EDTA | 0.10 g |
| Water | Balance |

TABLE 55

Styling gel

| Ingredient | 103 |
| --- | --- |
| PVP (LUVISKOL K 90 PULVER) | 2.00 g |
| NATROSOL 250 HHR | 0.50 g |
| Nanoemulsions of Examples 1-10 | 20.00 g |
| Eumulgin L | 0.20 g |
| Perfume | 0.15 g |
| UVINUL P 25 | 0.10 g |
| PHENOXYETHANOL | 0.20 g |
| PHB-METHYLESTER | 0.12 g |

TABLE 55-continued

Styling gel

| Ingredient | 103 |
| --- | --- |
| DISODIUM EDTA | 0.10 g |
| Water | Balance |

TABLE 56

Aerosol Styling mousse

| Ingredient | 104 |
| --- | --- |
| Polyquaternium-11 (GAFQUAT 755 N) | 15.00 g |
| Nanoemulsions of Examples 1-10 | 5.00 g |
| Laureth-4 | 0.40 g |
| Perfume | 0.15 g |
| PHENOXYETHANOL | 0.20 g |
| PHB-METHYLESTER | 0.12 g |
| DISODIUM EDTA | 0.10 g |
| Propane/Butane | 6.00 g |
| Water | Balance |

TABLE 57

Aerosol hairspray

| Ingredient | 105 |
| --- | --- |
| LUVISKOL VA 37 E | 8.00 g |
| Ethanol | 50.00 g |
| Surfactant 193 | 0.40 g |
| Perfume | 0.15 g |
| Nanoemulsions of Examples 1-10 | 5.00 g |
| Propane/Butane | 30.0 g |
| Water | Balance |

TABLE 58

Spray Gel

| Ingredient | 106 |
| --- | --- |
| Luviskol VA64 | 3.00 g |
| NATROSOL 250 HHR | 0.30 g |
| Nanoemulsions of Examples 1-10 | 20.00 g |
| Eumulgin L | 0.20 g |
| Perfume | 0.15 g |
| PHENOXYETHANOL | 0.20 g |
| PHB-METHYLESTER | 0.12 g |
| DISODIUM EDTA | 0.10 g |
| Water | Balance |

TABLE 59

Leave-on Conditioner

| Ingredient | 107 |
| --- | --- |
| JAGUAR C-17 | 0.30 g |
| NATROSOL 250 HHR | 0.30 g |
| Nanoemulsions of Examples 1-10 | 20.00 g |
| Eumulgin L | 0.20 g |
| Perfume | 0.15 g |
| PHENOXYETHANOL | 0.20 g |
| PHB-METHYLESTER | 0.12 g |
| DISODIUM EDTA | 0.10 g |
| Water | Balance |

TABLE 60

Rinse-off Conditioner

| Ingredient | 108 |
|---|---|
| CETEARYL ALCOHOL | 4.50 g |
| CETRIMONIUM CHLORIDE (GENAMIN CTAC 50) | 1.30 g |
| Citric acid | 0.30 g |
| Perfume | 0.15 g |
| Nanoemulsions of Examples 1-10 | 6.00 g |
| Water | Balance |

Trade Names Used in the Examples

Abilquat® 3270: Quaternium-80, 50% in propylene glycol (Goldschmidt)

Aculyn® 48: PEG-150/STEARYL ALCOHOL/SMDI COPOLYMER, 19% in water (Rohm and Haas)

AMP 95% Aminomethylpropanol, 95% aqueous solution

Amphomer® OCTYLACRYLAMIDE/ACRYLATES/BUTYLAMINOETHYL METHACRYLATE COPOLYMER

Aristoflex® AVC AMMONIUM ACRYLOYLDIMETHYLTAURATE/VP COPOLYMER

Aquaflex® FX-64: ISOBUTYLENE/ETHYLMALEIMIDE/HYDROXYETHYLMALEIMIDE COPOLYMER, 40% strength in water/ethanol (ISP)

Aquaflex SF 40: VP/VINYL CAPROLACTAM/DMAPA ACRYLATES COPOLYMER, 40% in ethanol (ISP)

Advantage® SVINYL CAPROLACTAM/VP/DIMETHYLAMINOETHYL METHACRYLATE COPOLYMER

Carbomer (Carbopol) Acrylic acid homopolymer

Celquat® L200: Copolymer of hydroxyethylcellulose and diallyldimethylammonium chloride; Polyquaternium-4

GENAMIN CTAC 50 CTFA: Cetrimonium Chloride; Cetyltrimethylammonium chloride Copolymer 845: VP/DIMETHYLAMINOETHYLMETHACRYLATE COPOLYMER, 20% in water (ISP)

Dehydol® LS 4 Lauryl alcohol tetraoxyethylen ether

Dekaben® LMB: IODOPROPYNYL BUTYLCARBAMATE, 10% strength in butylene glycol

Dekaben® LMP: Phenoxyethanol and iodopropynyl butylcarbamate

Diaformer Z-711: ACRYLATES/LAURYL ACRYLATE/STEARYL ACRYLATE/ETHYLAMINE OXIDE METHACRYLATE COPOLYMER, 40% (Clariant)

Dow Corning 1401: High molecular weight Dimethiconol, 13% in cyclomethicone

Eumulgin® L: INCI: PEG-1-PEG-9 LAURYL GLYCOL ETHER

Flexan® Sodium polystyrenesulfonate

GAFQUAT® 755 N CTFA: Polyquatemium-11

Jaguar C-17/162CTFA: GUAR HYDROXYPROPYLTRIMONIUM CHLORIDE

Laureth-4Lauryl alcohol tetraoxyethylen ether

Luviset® Clear: Terpolymer of vinylpyrrolidone, methacrylamide and vinylimidazole (BASF)

Luviskol® VA 64 Vinylpyrrolidone/vinylacetate copolymer

Luviskol® K 90 Powder Vinylpyrrolidone

Luvimer® 100 P t-butyl acrylate/ethyl acrylate/methacrylic acid copolymer

Natrosol® G: Hydroxyethylcellulose

Pemulen®: ACRYLATES/C10-30 ALKYL ACRYLATE CROSSPOLYMER

Structure® 3001: ACRYLATES/CETETH-20 ITACONATE COPOLYMER 30% strength in water (National Starch)

Surfactant 193: Ethoxylated dimethylpolysiloxane; INCI: PEG-12 Dimethicone (Dow Corning)

Synthalen® W 2000: ACRYLATES/PALMETH-25 ACRYLATE COPOLYMER (31% in water)

Tego Betain L 5045 CTFA: COCAMIDOPROPYL BETAINE

Test Methods

Time to Wick (T2W) Measurement Method

The fabric Time to Wick property is a measure of the water repellency or oil repellency of a fabric, where longer times indicate greater repellency. Water repellency is measured when a drop of water is applied to the fabric, whereas oil repellency is measured when a drop of oil is applied to the fabric. The Time to Wick value is measured as follows: The tests are conducted in a well-ventilated lab whose humidity is between 40 to 60% RH. and temperature is between 20 to 25° C. All samples are preconditioned for at least 24 hours in that lab prior to testing. Untreated control white cotton fabric is prepared from new, 100% cotton, woven, white bed sheets, which are de-sized by 3 rounds of laundering using the AATCC 2003 standard reference liquid detergent without optical brighteners (AATCC—American Association of Textile Chemists and Colorists, Research Triangle Park, N.C., USA), then cut to yield fabric pieces approximately 10 cm×10 cm in size. Treated test fabric is the same as the untreated control fabric plus the addition of the treatment being tested, which is applied to the fabric in accordance with the manufacturer's instructions, after the de-sizing steps.

On a flat, level hard surface (e.g. benchtop) is placed a fresh square of a paper towel at least 10 cm×10 cm in size, and on top of that is placed a square of the prepared fabric. A 300 μL drop of liquid is then dispensed onto the fabric surface from a calibrated pipettor. The drop is DI water when measuring water repellency or it is Canola Oil when measuring oil repellency—. The process of absorption of the liquid drop is visually monitored using a video camera such as a—Webcam Pro 9000 (Logitech, Silicon Valley, Calif., USA), integrated with a laptop computer, and displaying either an electronic timestamp or a stopwatch timer within the field of view, which counts the time elapsed in seconds. The imaging conditions are set up such that the margins of the drop and the fabric surface are both clearly visible and simultaneously in focus, with the viewing angle being from directly above. Nine drops are administered per fabric square, with each drop placed at a different location separate from all adjacent drops.

The recorded video is used to determine the time—at drop addition and the time—at drop absorption. For each drop, the time differential between those two time points is calculated and recorded. The time at drop addition is defined as being the earliest time point at which a portion of the drop is observed making contact with the surface of the fabric. The time at drop absorption is defined as being the earliest time point at which no portion of the drop is observed rising above the surface of the fabric. After 60 minutes, the video capture is terminated regardless of any remaining drops left unabsorbed. Such drops are recorded as having a time differential of 60 mins. The Time to Wick value for a given liquid on fabric is the average of the time differentials recorded for 9 drops of that liquid. In order to determine the effect of a treatment, comparisons are made between the average Time to Wick value obtained from the treated fabric, versus the average obtained from its untreated control fabric using the same liquid, where longer times indicate greater repellency.

Particle Size Measurement Test Method

Nanoemulsions were diluted with DI water to a concentration of 1% prior to making particle size measurements. The particle size measurements are made via dynamic light scattering on a model 3D-DLS spectrometer instrument (LS Instruments, Switzerland). The software accompanying the instrument (version 6.3, LS Instruments, Switzerland) is used to control the spectrometer to acquire data and conduct particle size analysis in dynamic light scattering mode. The instrument is set with the following conditions: Wavelength=632 nm (HeNe laser), scattering angle=90°, Temperature=297 Kelvin (measured by the instrument with sample placed in water bath and equilibrated for 10 minutes), Integration Time $T_{int}$=2 min, Count rate set between 100-250 kcps (attenuating the laser power), Lag time set between 0.7 microseconds to 50 seconds. All measurements were taken in autocorrelation mode. All data are reported as the second-order Cumulant fit to the autocorrelation function. The nanoemulsion's particle size is reported as the average diameter value measured, when calculated on a volume-weighted basis. A nanoemulsion whose particle size is less than 200 nm is defined as being a nanoemulsion.

Technical Drying Time Test Method

Switches of human hair, which are of straight low-lift medium brown Caucasian hair, approximately 20 cm long and having approximately 4 g of hair per switch, are obtained from International Hair Importers & Products (IHIP) (White Plains, N.Y., USA) for use in the Hair Drying Time Test. Use three switches of hair per treatment and per control. To prepare the hair, measure and record the initial dry weight of each hair switch, then wash each switch using the following shampoo and instructions. Hang the switches on a rod above a sink, and wet the hair with 38° C. DI water until saturated. Squeeze out excess water and apply the specified shampoo, at a dosage of 0.1 g shampoo per 1 g hair (dry wt). Apply half the total amount of shampoo on one side of the switch and rest on the other side. Massage the hair switches by hand for 60 seconds to create lather throughout the switch. Rinse thoroughly with 38° C. DI water running at 4 to 6 L/min for at least 2 minutes (1 min per side). Use hand manipulation to squeeze out the excess water. Up to 35 g of hair can be shampooed simultaneously. Each ingredient in the shampoo is listed below at its final concentration in percent by weight:

| Shampoo Ingredients | Wt % |
| --- | --- |
| Sodium Lauryl Sulfate | 5.0 |
| Sodium Laureth Sulfate | 10.0 |
| Cocamidopropyl betaine | 0.8 |
| Guar Cationic Polymer | 0.5 |
| Extracts of *Camellia Sinensis* Leaf, *Citrus Auranfium Dulcis* Flower, *Zea Mays* Silk. | 2.1 |
| Sodium Citrate | 0.4 |
| Sodium EDTA | 0.16 |
| Citric Acid | 0.04 |
| Sodium Benzoate | 0.25 |
| DI Water to balance to 100% | |

The remaining steps in the hair dying time test method are conducted in an air conditioned room having a temperature of 20 to 25° C., and a relative humidity of 40 to 60% RH, and are conducted in immediate succession without any delays or pauses between steps. Apply the treatment product being tested onto just one hair switch at a time, using switches prepared and shampooed as specified above. Prior to applying the treatment, ensure that the hair switch is thoroughly saturated with 38° C. DI water but is not dripping. Place the switch in a plastic weighing-boat dish approximately 13 cm×13 cm, and dose the wet hair with 1 g of the treatment solution being tested per 4 g of hair dry weight. Apply the treatment solution homogenously along the length of the hair. Massage the treatment solution into the hair switch in the dish for 3 minutes with hand manipulation, ensuring that all the hair fibers are exposed to the solution. The switch is then subjected to multiple cycles of blow drying and weighing, where the duration of blow drying and the subsequent switch weight are recorded for each cycle, and are compared to the switch's initial dry weight. Hang the hair switch vertically and commence blow drying while the hair is still thoroughly saturated with water and treatment solution. Blow dry the hair switch using a Sunbeam 1600 Watt hand-held electric hair dryer with diffuser nozzle adapter, with the heat level selection set on High, (Sunbeam Corporation Limited, Botany, Australia), and positioned 7 cm away from the hair. After 3 minutes of blow drying (1.5 mins per side), weigh the hair switch and record the weight. Press the hair switch gently between two kitchen paper towels for 2 seconds and reweigh. Repeatedly blow dry and reweigh the hair again using drying time increments of 30 seconds for each cycle. When the switch weight approaches its initial dry weight, reduce the drying time increments to 20 seconds for each subsequent cycle, and continue the drying and weighing cycles until the hair switch returns to its initial dry weight. The switch's total hair drying time is determined by summing all of the drying times that were required to return the hair to its initial dry weight. This cumulative value is the switch's Hair Drying Time. The hair drying times obtained from the three replicate switches in each treatment are averaged to determine the mean hair drying time for the treatment. To determine the effect of the treatment on hair drying time, the mean hair drying time for the treatment is compared to the mean hair drying time obtained from 3 control switches, which were each dosed with 1 g of DI water instead of 1 g of treatment solution.

The above Technical Dry Time Test Method is also relevant to skin.

Contact Angle Test Method

The static contact angle of a nanoemulsion is determined by measuring a sessile droplet of water placed on a nanoemulsion-coated surface, as measured via an optical profile image of the droplet. The surface is prepared using 2.5 cm×2.5 cm sized silica wafers (J#19777), as available from Silicon Valley Microelectronics Inc. (SVM), (Santa Clara, Calif., USA). Clean the wafers by rinsing with DI water followed by further rinses with ethanol and then with acetone, ensuring that both the organic solvents are of a high purity grade such as that suitable for use in LC-MS analyses. Expose the wafers to ozone for 15 minutes, by placing a cleaned wafer into a specimen chamber attached to an ozone generator such as the UV/Ozone Pro Cleaner™ (manufactured by Bioforce Nanoscience, Ames, Iowa, USA). The nanoemulsion to be tested is then spin-coated onto the cleaned and ozonated wafers. To achieve this coating, prepare the emulsion to be tested at a concentration of 500 ppm in DI water. Dispense 1600 μL of the nanoemulsion onto a silica wafer, wait 1 min then spin the wafer at 2000 rpm for 30 seconds in a spin coater instrument, such as the WS-400B-6NPP/Lite/AS2 (manufactured by Laurell Technology Corporation, North Wales, Pa., USA). The spin-coated wafer is the then allowed to cure for 24 hours at room temp or in an 80° C. oven for 1 hour. With the wafer at room temperature, use a contact angle goniometer such as the FTA 200 manufactured by First Ten Angstroms, Inc, Portsmouth, Va., USA), to measure the static contact angle of a sessile 10 µL drop of DI water placed onto the coated surface of the silica wafer. Prepare and measure 3 replicate spin-coated wafers for each nanoemulsion to be tested, and average the replicate contact angle results to obtain the contact angle for that nanoemulsion. The contact angle of the cleaned but uncoated silica wafer is 36°.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An amino silicone nanoemulsion comprising:
  a. one or more liquid amino silicone compounds represented by formula (1) below:

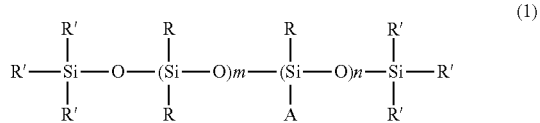

where each R is independently selected from an alkyl group having 1-10 carbon atoms, or a phenyl group, wherein each R' is independently selected from an alkyl group having 1-10 carbon atoms, a phenyl group, a monovalent group represented by formula (2) below, or a monovalent group represented by the formula: —$OR^3$, where $R^3$ is independently selected from a hydrogen atom or a monovalent hydrocarbon group with 1-10 carbon atoms;
  m is a whole number from 50-1000,
  n is a whole number from 1-100,
  where m/n is from 49 to 100,
  A is a monovalent group represent by formula (2) below:

where each $R^1$ and $R^2$ are independently selected from divalent hydrocarbon groups with 1-10 carbon atoms;
  a is a whole number from 0-4;

b. from about 0.1% to about 20%, by weight of said amino silicone compound, of a solvent selected from the group consisting of a diethylene glycol monoalkyl ether that has an alkyl group having 4-12 carbon atoms, or a mixture thereof;
  c. from about 1% to about 40% by weight of said amino silicone compound of a surfactant; and
  d. a protonating agent; and
  wherein the sum of the solvent and the surfactant is less than 45% by weight of said amino silicone compound; and
  wherein said amino silicone nanoemulsion is free of a silicone resin.

2. An amino silicone nanoemulsion according to claim 1, wherein the average particle size of said nanoemulsion is from about 20 nm to about 350 nm.

3. An amino silicone nanoemulsion according to claim 1, wherein the sum of the solvent and the surfactant is less than 32% by weight of said amino silicone compound.

4. An amino silicone nanoemulsion according to claim 1, wherein said amino silicone nanoemulsion comprises from about 0.1% to about 12%, by weight of said amino silicone compound, of said solvent.

5. An amino silicone nanoemulsion according to claim 1, wherein said amino silicone nanoemulsion comprises from about 0.1% to about 5%, by weight of said amino silicone compound, of said solvent.

6. An amino silicone nanoemulsion according to claim 1, wherein said amino silicone nanoemulsion comprises from about 1% to about 30%, by weight of said amino silicone compound, of said surfactant.

7. An amino silicone nanoemulsion according to claim 1, wherein the pH of the amino silicone nanoemulsion is less than 7.0.

8. An amino silicone nanoemulsion according to claim 1, wherein in said formula (1), R is a methyl group, $R^1$ and $R^2$ are alkyl groups having 1-3 carbon atoms.

9. An amino silicone nanoemulsion according to claim 1, wherein in said formula (1), m/n is from 55 to 100.

10. An amino silicone nanoemulsion according to claim 1, wherein in said formula (1), m/n is from 55 to 90.

11. An amino silicone nanoemulsion according to claim 1, wherein in said formula (1), m/n is from 55 to 80.

12. An amino silicone nanoemulsion according to claim 1, wherein from about 1% to about 20% of the terminal R' groups are monovalent groups represented by the formula: —$OR^3$, where $R^3$ is a hydrogen atom or a monovalent hydrocarbon group with 1-10 carbon atoms.

13. An amino silicone nanoemulsion according to claim 1, wherein said solvent is selected from the group consisting of diethylene glycol monohexyl ether, diethylene glycol monobutyl ether, or a mixture thereof.

14. An amino silicone nanoemulsion according to claim 1, wherein said surfactant is selected from nonionic surfactant, anionic surfactant, cationic surfactant, zwitterionic surfactant, ampholytic surfactant, amphoteric surfactant or a mixture thereof.

15. An amino silicone nanoemulsion according to claim 1, wherein said surfactant is a nonionic surfactant.

16. A treatment composition that comprises
  a. an amino silicone nanoemulsion according to claim 1,
  b. a carrier,
  wherein said treatment composition comprises from about 0.001% to about 15% amino silicone nanoemulsion, by weight of the treatment composition, and said treatment composition is free of silicone resin.

17. The treatment composition of claim 16, wherein said treatment composition is selected from the group consisting of beauty care composition, hand washing composition, body wash composition, shampoo composition, conditioner composition, cosmetic composition, hair removal composition, oral care composition, laundry spray composition, laundry rinse additive composition, liquid laundry detergent compositions, solid laundry detergent compositions, hard surface cleaning compositions, liquid hand dishwashing compositions, solid automatic dishwashing compositions, liquid automatic dishwashing, and tab/unit dose form automatic dishwashing compositions, and laundry detergent compositions contained in a water-soluble pouch.

18. A treatment composition according to claim 16, wherein said composition further comprises a perfume.

19. A treatment composition according to claim 16, wherein said composition further comprises a detersive surfactant.

20. A treatment composition according to claim 19, wherein said detersive surfactant comprises one or more surfactants selected from nonionic surfactants, cationic surfactants, anionic surfactants, zwitterionic surfactants, ampholytic surfactants, or amphoteric surfactants.

21. A treatment composition according to claim 19, wherein said detersive surfactant comprises a surfactant selected from $C_{10}$-$C_{16}$ alkyl benzene sulfonates, $C_8$-$C_{18}$ alkyl sulfate, $C_8$-$C_{18}$ alkyl ethoxylated sulfate, or a mixture thereof.

22. A treatment implement comprising a nonwoven substrate and the treatment composition according to claim 16.

* * * * *